United States Patent [19]

Benton et al.

[11] Patent Number: 5,227,556
[45] Date of Patent: Jul. 13, 1993

[54] TURBULENT FLOW PROCESS, MONOALKYL AROMATIC PRODUCTION PROCESS AND REACTOR FOR SUCH PROCESS

[75] Inventors: James H. Benton, Surgar Land; John B. Ivy, Lake Jackson; Jack Broodo, Missouri City; Kirk A. Leissner, Angleton; Ellroy G. Fox, Clute, all of Tex.

[73] Assignee: The Dow Chemical Company, Midland, Mich.

[21] Appl. No.: 511,489

[22] Filed: Apr. 17, 1990

[51] Int. Cl.⁵ .............................. C07C 2/70; B01J 8/04
[52] U.S. Cl. .................... 585/323; 585/461; 585/474; 422/196; 422/197; 422/198; 422/200; 422/201
[58] Field of Search ............... 585/323, 461, 474; 422/196, 197, 198, 200, 201

[56] References Cited

U.S. PATENT DOCUMENTS

| | | | |
|---|---|---|---|
| 2,139,943 | 12/1938 | Fenske et al. | 422/197 |
| 2,429,622 | 10/1947 | Hirsch | 585/323 |
| 2,491,618 | 12/1949 | Luetzelschwab | 422/201 |
| 3,121,123 | 2/1964 | Sharman | 585/474 |
| 3,200,164 | 8/1965 | Gerald | 585/323 |
| 3,212,860 | 10/1965 | Vernon | 422/201 |
| 3,448,161 | 6/1969 | Garcia et al. | 260/671 |
| 3,501,536 | 3/1970 | Borst, Jr. | 260/683.48 |
| 3,541,174 | 11/1970 | Inoue et al. | 260/672 |
| 3,551,510 | 12/1920 | Pollitzer et al. | 585/474 |
| 3,674,885 | 7/1972 | Griesinger et al. | 585/323 |
| 3,683,043 | 8/1972 | Ghirga et al. | 585/323 |
| 3,696,168 | 10/1972 | Vanderveen | 260/683.58 |
| 3,751,232 | 8/1973 | Borre et al. | 23/288 R |
| 3,763,022 | 10/1973 | Chapman | 585/410 |
| 3,766,290 | 10/1973 | Carlson | 260/672 T |
| 3,817,708 | 4/1972 | Vernon | 23/260 |
| 3,830,864 | 8/1974 | Borre et al. | 260/669 R |
| 3,839,548 | 10/1974 | Jackson | 422/198 |
| 3,848,012 | 11/1974 | Applegath et al. | 260/671 R |
| 3,856,878 | 12/1974 | Messina et al. | 260/671 C |
| 3,882,183 | 5/1975 | Messina et al. | 260/671 R |
| 3,914,110 | 10/1975 | Anderson | 23/288 E |
| 3,914,111 | 10/1975 | Anderson | 23/288 E |
| 4,169,111 | 9/1979 | Wight | 585/474 |
| 4,179,473 | 12/1979 | Cox | 585/313 |

OTHER PUBLICATIONS

Unit Processes and Principles of Chemical Engineering, John C. Olsen, Jul. 1932.

Primary Examiner—Theodore Morris

[57] ABSTRACT

A process for turbulently flowing together reactants in uniform proportions in a reactor vessel. A process for producing ethylbenzene by reacting ethylene and benzene in the presence of a catalyst in a reactor vessel from which useful heat generated by the reaction is transferred to a heat transfer medium flowing through the reactor and in which the reaction occurs in a relatively short time period. In one embodiment, polyethylbenzenes produced in the reactor vessel are not recycled into the vessel. A reactor for a reaction of reactant materials that are uniformly and turbulently mixed together.

12 Claims, 14 Drawing Sheets

FIG. 11

| SHELL | | TUBE | | | |
|---|---|---|---|---|---|
| 0" | 127.1 | 0" | 194.8 | 76" | 211.2 |
| 4" | 128.3 | 2" | 194.8 | 78" | 209.9* |
| 8" | 129.2* | 4" | 194.6 | 80" | 208.6 |
| 12" | 130.0 | 6" | 194.4 | 82" | 206.9 |
| 16" | 130.6 | 8" | 194.4 | 84" | 211.2 |
| 20" | 132.9 | 10" | 193.6 | 86" | 209.4* |
| 24" | 134.8 | 12" | 193.8 | 88" | 207.6* |
| 28" | 141.7 | 14" | 194.5 | 90" | 205.7 |
| 32" | 145.4 | 16" | 196.8 | 92" | 207.0* |
| 36" | 154.8 | 18" | 196.1 | 94" | 208.2 |
| 40" | 160.9 | 20" | 192.3 | 96" | 207.1* |
| 44" | 160.7 | 22" | 194.8 | 98" | 206.1 |
| 48" | 159.5 | 24" | 196.6* | 100" | 206.2* |
| 52" | 158.3 | 26" | 198.4 | 102" | 206.3 |
| 56" | 160.3 | 28" | 195.0 | 104" | 207.7* |
| 60" | 162.7 | 30" | 197.0 | 106" | 209.2 |
| 64" | 160.6 | 32" | 200.0 | 108" | 208.2* |
| 68" | 158.6 | 34" | 199.1 | 110" | 207.2 |
| 72" | 156.5 | 36" | 197.0 | 112" | 207.6* |
| 76" | 155.1 | 38" | 200.3 | 114" | 208.1 |
| 80" | 154.8 | 40" | 201.6* | 116" | 207.8* |
| 84" | 157.4 | 42" | 203.0 | 118" | 207.5 |
| 88" | 156.9* | 44" | 202.0 | 120" | 207.6* |
| 92" | 156.5 | 46" | 204.8 | 122" | 207.7 |
| 96" | 155.1* | 48" | 205.3 | 124" | 207.8* |
| 100" | 153.6 | 50" | 206.1 | 126" | 207.9 |
| 104" | 156.7* | 52" | 206.5 | 128" | 208.4* |
| 108" | 159.8 | 54" | 206.9 | 130" | 208.9 |
| 112" | 161.5* | 56" | 207.5* | 132" | 209.1* |
| 116" | 163.1 | 58" | 208.0 | 134" | 209.2 |
| 120" | 160.2* | 60" | 208.5 | 136" | 209.5* |
| 124" | 157.4 | 62" | 208.8 | 138" | 209.9 |
| 128" | 158.0* | 64" | 207.3 | 140" | 210.2* |
| 132" | 158.7 | 66" | 208.5 | 142" | 210.6 |
| 136" | 157.7* | 68" | 208.7* | 144" | 210.6* |
| 140" | 156.7 | 70" | 208.9 | 146" | 210.5 |
| 144" | 156.1* | 72" | 206.8 | 148" | 210.9* |
| 148" | 155.4 | 74" | 208.0 | 150" | 211.3 |

CONTROL TEMPERATURES (CELSIUS)

TE-371  ETHYLENE        40.9            TE-375  AE-1 AROMATIC     196.0

FLOWS
BENZENE       2247.0 #/HR

ETHYLENE       89.9 #/HR
SHELL        2258.0 #/HR
'RED OIL'      18.6 #/HR

|  | FEED | | PRODUCT | |
| --- | --- | --- | --- | --- |
|  | WEIGHT% | MOLE% | WEIGHT% | MOLE% |
| ETHYLENE | 3.82385 | 10.07955 | 0.00000 | 0.00000 |
| UNIDENTIFIED | 1.75699 | 2.59857 | 1.64192 | 2.69848 |
| BENZENE | 85.47470 | 80.92187 | 77.62641 | 81.66578 |
| METHYLCYCLOHEXANE | 0.00301 | 0.00229 | 0.13291 | 0.11245 |
| TOLUENE | 0.56605 | 0.45435 | 0.49352 | 0.44019 |
| UNIDENTIFIED | 0.21574 | 0.15954 | 0.09933 | 0.08163 |
| ETHYLBENZENE | 7.50299 | 5.22598 | 16.04497 | 12.41865 |
| CUMENE | 0.00347 | 0.00214 | 0.00641 | 0.00438 |
| n-PROPYLBENZENE | 0.00998 | 0.00614 | 0.01367 | 0.00935 |
| m-ETHYLTOLUENE | 0.00626 | 0.00385 | 0.04885 | 0.03340 |
| p-ETHYLTOLUENE | 0.00021 | 0.00013 | 0.02941 | 0.02011 |
| o-ETHYLTOLUENE | 0.00010 | 0.00006 | 0.04456 | 0.03046 |
| Iso-BUTYLBENZENE | 0.00946 | 0.00521 | 0.01893 | 0.01159 |
| sec-BUTYLBENZENE | 0.00310 | 0.00171 | 0.04531 | 0.02774 |
| m-DIETHYLBENZENE | 0.02456 | 0.01353 | 1.50422 | 0.92101 |
| p-DIETHYLBENZENE | 0.00772 | 0.00425 | 0.72177 | 0.44193 |
| o-DIETHYLBENZENE | 0.00059 | 0.00033 | 0.45638 | 0.27943 |
| DIETHYLTOLUENES | 0.00744 | 0.00371 | 0.00000 | 0.00000 |
| m-ETHYLCUMENE | 0.00016 | 0.00008 | 0.00000 | 0.00000 |
| p-ETHYLCUMENE | 0.00005 | 0.00003 | 0.00000 | 0.00000 |
| o-ETHYLCUMENE | 0.00000 | 0.00000 | 0.00000 | 0.00000 |
| m-ETHYL-n-PROPYLBENZENE | 0.00090 | 0.00045 | 0.00396 | 0.00219 |
| p-ETHYL-n-PROPYLBENZENE | 0.00043 | 0.00021 | 0.01070 | 0.00593 |
| o-ETHYL-n-PROPYLBENZENE | 0.00004 | 0.00002 | 0.00000 | 0.00000 |
| TETRALIN | 0.00150 | 0.00084 | 0.00836 | 0.00520 |
| m-ETHYL-iso-BUTYLBENZENE | 0.00102 | 0.00047 | 0.00840 | 0.00425 |
| p-ETHYL-iso-BUTYLBENZENE | 0.00047 | 0.00022 | 0.00242 | 0.00123 |
| o-ETHYL-iso-BUTYLBENZENE | 0.00001 | 0.00001 | 0.00000 | 0.00000 |
| m-ETHYL-sec-BUTYLBENZENE | 0.00062 | 0.00028 | 0.00000 | 0.00000 |
| p-ETHYL-sec-BUTYLBENZENE | 0.00017 | 0.00008 | 0.00242 | 0.00123 |
| o-ETHYL-sec-BUTYLBENZENE | 0.00003 | 0.00001 | 0.00000 | 0.00000 |
| UNIDENTIFIED | 0.09748 | 0.05545 | 0.01213 | 0.00767 |
| 135-TRIETHYLBENZENE | 0.08954 | 0.04081 | 0.33453 | 0.16941 |
| 124-TRIETHYLBENZENE | 0.00034 | 0.00016 | 0.16588 | 0.08400 |
| 123-TRIETHYLBENZENE | 0.00013 | 0.00006 | 0.00000 | 0.00000 |
| DIETHYLCUMENES | 0.00000 | 0.00000 | 0.00000 | 0.00000 |
| DIETHYL-n-PROPYLBENZENES | 0.00000 | 0.00000 | 0.00000 | 0.00000 |
| PHENYLCYCLOHEXANE | 0.00000 | 0.00000 | 0.00000 | 0.00000 |
| DIETHYL-iso-BUTYLBENZENES | 0.00000 | 0.00000 | 0.00000 | 0.00000 |
| DIETHYL-sec-BUTYLBENZENES | 0.00000 | 0.00000 | 0.00000 | 0.00000 |
| 1235-TETRAETHYLBENZENE | 0.00000 | 0.00000 | 0.06158 | 0.02659 |
| 1245-TETRAETHYLBENZENE | 0.00000 | 0.00000 | 0.05626 | 0.02429 |
| 1234-TETRAETHYLBENZENE | 0.00000 | 0.00000 | 0.00000 | 0.00000 |
| DIPHENYLMETHANE | 0.00000 | 0.00000 | 0.00000 | 0.00000 |
| UNIDENTIFIED | 0.02536 | 0.01172 | 0.00987 | 0.00507 |
| 1,1 DIPHENYLETHANE | 0.00581 | 0.00236 | 0.03251 | 0.01466 |
| 1,2 DIPHENYLETHANE | 0.00000 | 0.00000 | 0.00000 | 0.00000 |
| PENTAETHYLBENZENE | 0.00000 | 0.00000 | 0.00000 | 0.00000 |
| HEXAETHYLBENZENE | 0.00000 | 0.00000 | 0.00000 | 0.00000 |
| ETHYLDIPHENYLETHANE | 0.00000 | 0.00000 | 0.00391 | 0.00153 |
| UNIDENTIFIED | 0.00961 | 0.00309 | 0.00000 | 0.00000 |
| ALUMNIUM CHLORIDE | 0.21014 | 0.11654 | 0.21854 | 0.13468 |
| HYDROGEN CHLORIDE | 0.13995 | 0.28393 | 0.13995 | 0.31550 |
| WATER | 0.00000 | 0.00000 | 0.00000 | 0.00000 |

| COMPOUND | R-1 FEED WEIGHT% | PASS 1 WEIGHT% | PASS 2 WEIGHT% | PASS 3 WEIGHT% | PASS 4 WEIGHT% | PASS 5 WEIGHT% | PASS 6 WEIGHT% | PASS 7 WEIGHT% | PASS 8 WEIGHT% |
|---|---|---|---|---|---|---|---|---|---|
| ETHYLENE | 0.0000 | 0.0694 | 0.1829 | 0.2716 | 0.7031 | 0.2132 | 0.7133 | 0.2769 | 0.3289 |
| UNIDENTIFIED | 2.3539 | 2.4564 | 2.3898 | 2.3738 | 2.3447 | 2.3304 | 2.2837 | 2.2747 | 1.9280 |
| BENZENE | 93.6510 | 88.3679 | 83.5831 | 79.0920 | 75.6094 | 70.9171 | 68.0705 | 64.0364 | 60.9738 |
| METHYLCYCLOHEXANE | 0.1795 | 0.1767 | 0.1728 | 0.1701 | 0.1674 | 0.1656 | 0.1629 | 0.1602 | 0.1605 |
| TOLUENE | 0.1952 | 0.1808 | 0.1634 | 0.1481 | 0.1358 | 0.1236 | 0.1153 | 0.1025 | 0.0922 |
| UNIDENTIFIED | 0.1379 | 0.1361 | 0.1342 | 0.1326 | 0.1297 | 0.1287 | 0.1257 | 0.1251 | 0.2253 |
| CUMENE | 0.0000 | 0.0000 | 0.0000 | 0.0000 | 0.0000 | 0.0000 | 0.0000 | 0.0000 | 0.0000 |
| n-PROPYLBENZENE | 0.0037 | 0.0000 | 0.0122 | 0.0143 | 0.0167 | 0.0181 | 0.0199 | 0.0199 | 0.0237 |
| m-ETHYLTOLUENE | 0.0000 | 0.0070 | 0.0086 | 0.0111 | 0.0120 | 0.0136 | 0.0136 | 0.0142 | 0.0152 |
| p-ETHYLTOLUENE | 0.0000 | 0.0000 | 0.0000 | 0.0000 | 0.0000 | 0.0000 | 0.0000 | 0.0000 | 0.0000 |
| o-ETHYLTOLUENE | 0.0000 | 0.0069 | 0.0144 | 0.0195 | 0.0210 | 0.0232 | 0.0226 | 0.0237 | 0.0243 |
| iso-BUTYLBENZENE | 0.0057 | 0.0047 | 0.0046 | 0.0040 | 0.0042 | 0.0033 | 0.0034 | 0.0031 | 0.0032 |
| sec-BUTYLBENZENE | 0.0060 | 0.0164 | 0.0250 | 0.0285 | 0.0340 | 0.0379 | 0.0448 | 0.0482 | 0.0572 |
| m-DIETHYLBENZENE | 0.1343 | 0.3170 | 0.6851 | 1.0450 | 1.5035 | 2.0630 | 2.5759 | 3.1112 | 3.9029 |
| p-DIETHYLBENZENE | 0.0630 | 0.1930 | 0.4090 | 0.6799 | 0.8948 | 1.2734 | 1.4532 | 1.8352 | 2.0914 |
| o-DIETHYLBENZENE | 0.0120 | 0.1787 | 0.3818 | 0.7235 | 0.8393 | 1.2790 | 1.2815 | 1.7237 | 1.6667 |
| DIETHYLTOLUENES | 0.0000 | 0.0000 | 0.0000 | 0.0000 | 0.0000 | 0.0000 | 0.0000 | 0.0000 | 0.0000 |
| m-ETHYLCUMENE | 0.0000 | 0.0000 | 0.0000 | 0.0000 | 0.0000 | 0.0000 | 0.0000 | 0.0000 | 0.0000 |
| p-ETHYLCUMENE | 0.0000 | 0.0000 | 0.0000 | 0.0000 | 0.0000 | 0.0000 | 0.0000 | 0.0000 | 0.0000 |
| o-ETHYLCUMENE | 0.0000 | 0.0000 | 0.0000 | 0.0000 | 0.0000 | 0.0000 | 0.0000 | 0.0000 | 0.0000 |
| m-ETHYL-n-PROPYLBENZENE | 0.0000 | 0.0000 | 0.0000 | 0.0000 | 0.0051 | 0.0059 | 0.0081 | 0.0089 | 0.0127 |
| p-ETHYL-n-PROPYLBENZENE | 0.0000 | 0.0000 | 0.0000 | 0.0000 | 0.0000 | 0.0000 | 0.0000 | 0.0000 | 0.0000 |
| o-ETHYL-n-PROPYLBENZENE | 0.0000 | 0.0000 | 0.0000 | 0.0035 | 0.0042 | 0.0011 | 0.0000 | 0.0039 | 0.0040 |
| TETRALIN | 0.0000 | 0.0000 | 0.0000 | 0.0000 | 0.0000 | 0.0000 | 0.0058 | 0.0074 | 0.0065 |
| m-ETHYL-iso-BUTYLBENZENE | 0.0000 | 0.0000 | 0.0000 | 0.0000 | 0.0000 | 0.0000 | 0.0000 | 0.0000 | 0.0025 |
| p-ETHYL-iso-BUTYLBENZENE | 0.0000 | 0.0000 | 0.0000 | 0.0000 | 0.0000 | 0.0000 | 0.0000 | 0.0000 | 0.0000 |
| o-ETHYL-iso-BUTYLBENZENE | 0.0000 | 0.0000 | 0.0000 | 0.0000 | 0.0000 | 0.0000 | 0.0000 | 0.0000 | 0.0000 |
| m-ETHYL-sec-BUTYLBENZENE | 0.0000 | 0.0000 | 0.0000 | 0.0000 | 0.0000 | 0.0000 | 0.0000 | 0.0000 | 0.0025 |
| p-ETHYL-sec-BUTYLBENZENE | 0.0000 | 0.0000 | 0.0000 | 0.0000 | 0.0000 | 0.0000 | 0.0000 | 0.0000 | 0.0000 |
| o-ETHYL-sec-BUTYLBENZENE | 0.0000 | 0.0000 | 0.0000 | 0.0000 | 0.0000 | 0.0000 | 0.0000 | 0.0000 | 0.0000 |
| UNIDENTIFIED | 0.0000 | 0.0000 | 0.0000 | 0.0000 | 0.0037 | 0.0111 | 0.0124 | 0.0150 | 0.0168 |

FIG. 14

| | | | | | | | | |
|---|---|---|---|---|---|---|---|---|
| 1,3,5-TRIETHYLBENZENE | 0.0091 | 0.0735 | 0.1582 | 0.2711 | 0.4657 | 0.7240 | 0.9866 | 1.3388 | 1.8349 |
| 1,2,4-TRIETHYLBENZENE | 0.0000 | 0.0493 | 0.1161 | 0.2587 | 0.3447 | 0.6199 | 0.7158 | 1.0916 | 1.2300 |
| 1,2,3-TRIETHYLBENZENE | 0.0000 | 0.0000 | 0.0000 | 0.0047 | 0.0061 | 0.0126 | 0.0140 | 0.0236 | 0.0259 |
| DIETHYLCUMENES | 0.0000 | 0.0000 | 0.0000 | 0.0000 | 0.0000 | 0.0000 | 0.0000 | 0.0000 | 0.0000 |
| DIETHYL-n-PROPYLBENZENES | 0.0000 | 0.0000 | 0.0000 | 0.0000 | 0.0000 | 0.0000 | 0.0000 | 0.0000 | 0.0000 |
| PHENYLCYCLOHEXANE | 0.0000 | 0.0000 | 0.0000 | 0.0000 | 0.0000 | 0.0000 | 0.0000 | 0.0000 | 0.0000 |
| DIETHYL-iso-BUTYLBENZENES | 0.0000 | 0.0000 | 0.0000 | 0.0000 | 0.0000 | 0.0000 | 0.0000 | 0.0000 | 0.0000 |
| DIETHYL-sec-BUTYLBENZENES | 0.0000 | 0.0117 | 0.0391 | 0.0967 | 0.1491 | 0.2233 | 0.2702 | 0.4767 | 0.5261 |
| 1,2,3,5-TETRAETHYLBENZENE | 0.0000 | 0.0000 | 0.0000 | 0.0000 | 0.0000 | 0.3051 | 0.3692 | 0.6445 | 0.7232 |
| 1,2,4,5-TETRAETHYLBENZENE | 0.0000 | 0.0000 | 0.0000 | 0.0000 | 0.0000 | 0.0000 | 0.0036 | 0.0036 | 0.0036 |
| 1,2,3,4-TETRAETHYLBENZENE | 0.0000 | 0.0000 | 0.0000 | 0.0000 | 0.0000 | 0.0000 | 0.0000 | 0.0000 | 0.0000 |
| DIPHENYLMETHANE | 0.0000 | 0.0164 | 0.0326 | 0.0772 | 0.1169 | 0.0060 | 0.0170 | 0.0238 | 0.0281 |
| UNIDENTIFIED | 0.0000 | 0.0119 | 0.0130 | 0.0149 | 0.0166 | 0.0193 | 0.0226 | 0.0272 | 0.0367 |
| 1,1-DIPHENYLETHANE | 0.0000 | 0.0000 | 0.0000 | 0.0000 | 0.0000 | 0.0000 | 0.0000 | 0.0000 | 0.0000 |
| 1,2-DIPHENYLETHANE | 0.0000 | 0.0000 | 0.0000 | 0.0000 | 0.0000 | 0.0000 | 0.0000 | 0.0000 | 0.0000 |
| PENTAETHYLBENZENE | 0.0000 | 0.0000 | 0.0000 | 0.0000 | 0.0000 | 0.0000 | 0.0000 | 0.0000 | 0.0000 |
| HEXAETHYLBENZENE | 0.0000 | 0.0000 | 0.0000 | 0.0000 | 0.0000 | 0.0011 | 0.0000 | 0.0000 | 0.0097 |
| ETHYLDIPHENYLMETHANE | 0.0000 | 0.0000 | 0.0000 | 0.0000 | 0.0000 | 0.0000 | 0.0000 | 0.0000 | 0.0000 |
| UNIDENTIFIED | 0.0573 | 0.0014 | 0.0076 | 0.0748 | 0.0736 | 0.0725 | 0.0714 | 0.0703 | 0.0693 |
| ALUMINUM CHLORIDE | 0.0786 | 0.0773 | 0.0760 | 0.0911 | 0.0897 | 0.0883 | 0.0870 | 0.0857 | 0.0844 |
| HYDROGEN CHLORIDE | 0.0957 | 0.0941 | 0.0926 | 0.0911 | | | | | |
| WATER | 0.0011 | 0.0000 | 0.0000 | 0.0000 | 0.0000 | 0.0000 | 0.0000 | 0.0000 | 0.0000 |

FIG. 14 (continued)

| COMPOUND | R-1 FEED WEIGHT% | PASS 1 WEIGHT% | PASS 2 WEIGHT% | PASS 3 WEIGHT% | PASS 4 WEIGHT% | PASS 5 WEIGHT% | PASS 6 WEIGHT% | PASS 7 WEIGHT% | PASS 8 WEIGHT% |
|---|---|---|---|---|---|---|---|---|---|
| UNIDENTIFIED 1 | 0.830 | 0.820 | 0.820 | 0.800 | 0.800 | 0.780 | 0.770 | 0.770 | 0.730 |
| BENZENE | 97.765 | 91.484 | 86.821 | 82.277 | 77.286 | 71.993 | 68.543 | 65.888 | 59.316 |
| METHLCYCLOHEXANE | .188 | .187 | .186 | .184 | .181 | .177 | .176 | .173 | .167 |
| TOLUENE | .338 | .327 | .323 | .320 | .313 | .310 | .302 | .299 | .291 |
| UNIDENTIFIED 2 | 0.220 | 0.200 | 0.180 | 0.170 | 0.160 | 0.150 | 0.140 | 0.130 | 0.120 |
| ETHYLBENZENE | .359 | 6.249 | 10.124 | 13.482 | 16.684 | 19.764 | 21.468 | 22.564 | 24.890 |
| CUMENE | 0.000 | 0.000 | 0.000 | 0.000 | 0.000 | 0.000 | 0.000 | 0.000 | 0.000 |
| N-PROPYLBENZENE | 0.000 | 0.000 | 0.000 | 0.000 | 0.000 | 0.000 | 0.000 | 0.000 | 0.000 |
| M-ETHYLTOLUENE | 0.000 | .005 | .008 | .010 | .014 | .015 | .014 | .014 | .014 |
| P-ETHYLTOLUENE | 0.000 | 0.000 | 0.000 | 0.000 | .012 | .013 | 0.000 | 0.000 | 0.000 |
| O-ETHYLTOLUENE | 0.000 | .009 | .014 | .018 | .021 | .023 | .024 | .024 | .025 |
| ISO-BUTYLBENZENE | .015 | .025 | .003 | .003 | 0.000 | 0.000 | .003 | .003 | .002 |
| SEC-BUTYLBENZENE | 0.000 | 0.000 | .031 | .039 | .003 | .003 | .064 | .070 | .083 |
| M-DIETHYLBENZENE | .081 | .198 | .426 | .764 | 1.200 | 1.691 | 2.125 | 2.512 | 3.139 |
| P-DIETHYLBENZENE | .026 | .135 | .322 | .575 | .926 | 1.321 | 1.603 | 1.827 | 2.421 |
| O-DIETHYLBENZENE | .012 | .147 | .390 | .705 | 1.159 | 1.663 | 1.956 | 2.174 | 2.962 |
| DI-ETHYL-TOL | 0.000 | 0.000 | 0.000 | 0.000 | 0.000 | 0.000 | 0.000 | 0.000 | 0.000 |
| M-ETHYLCUMENE | 0.000 | 0.000 | 0.000 | 0.000 | 0.000 | 0.000 | 0.000 | 0.000 | 0.000 |
| P-ETHYLCUMENE | 0.000 | 0.000 | 0.000 | 0.000 | 0.000 | 0.000 | 0.000 | 0.000 | 0.000 |
| O-ETHYLCUMENE | 0.000 | 0.000 | 0.000 | 0.000 | 0.000 | 0.000 | 0.000 | 0.000 | 0.000 |
| M-ETHYL-N-PROPYL | 0.000 | 0.000 | 0.000 | 0.000 | 0.000 | 0.000 | .004 | .005 | .005 |
| P-ETHYL-N-PROPYL | 0.000 | 0.000 | 0.000 | 0.000 | 0.000 | 0.000 | 0.000 | 0.000 | 0.000 |
| O-ETHYL-N-PROPYL | 0.000 | 0.000 | 0.000 | 0.000 | .002 | .003 | 0.000 | 0.000 | 0.000 |
| TETRALIN | 0.000 | 0.000 | 0.000 | .003 | .004 | .005 | .003 | .003 | .004 |
| M-ETHYL-ISO-BUTY | 0.000 | 0.000 | 0.000 | 0.000 | .004 | .005 | .006 | .007 | 0.000 |
| P-ETHYL-ISO-BUTY | .003 | .003 | .004 | .003 | .007 | .010 | .012 | .012 | .018 |
| O-ETHYL-ISO-BUTY | 0.000 | 0.000 | 0.000 | 0.000 | 0.000 | 0.000 | 0.000 | 0.000 | .010 |
| M-ETHYL-SEC-BUTY | 0.000 | 0.000 | 0.000 | 0.000 | 0.000 | 0.000 | .007 | .007 | 0.000 |
| P-ETHYL-SEC-BUTY | 0.000 | 0.000 | 0.000 | 0.000 | .004 | .006 | 0.000 | 0.000 | 0.000 |
| O-ETHYL-SEC-BUTY | 0.000 | 0.000 | 0.000 | 0.000 | 0.000 | 0.000 | 0.000 | 0.000 | 0.000 |

FIG. 15

| | | | | | | | | | |
|---|---|---|---|---|---|---|---|---|---|
| UNIDENTIFIED 3 | 0.000 | 0.000 | 0.000 | 0.010 | 0.050 | 0.060 | 0.010 | 0.010 | 0.020 |
| 135-TRIETHYLBENZ | .068 | .063 | .093 | .168 | .279 | .438 | .624 | .904 | 1.115 |
| 124-TRIETHYLBENZ | .005 | .044 | 0.000 | 0.000 | 0.000 | 0.000 | 1.065 | 1.225 | 2.089 |
| 123-TRIETHYLBENZ | 0.000 | 0.000 | .108 | .235 | .477 | .816 | .031 | .030 | .070 |
| DIETHYLCUMENES | 0.000 | 0.000 | 0.000 | .005 | .013 | .023 | 0.000 | 0.000 | 0.000 |
| DIETHYL-N-PROPYL | 0.000 | 0.000 | 0.000 | 0.000 | 0.000 | 0.000 | 0.000 | 0.000 | 0.000 |
| PHENYLCYCLOHEXAN | 0.000 | 0.000 | 0.000 | 0.000 | 0.000 | 0.000 | 0.000 | 0.000 | 0.000 |
| DIETHYL-ISO-BUTY | 0.000 | 0.000 | 0.000 | .004 | .004 | .005 | .005 | .005 | .006 |
| DIETHYL-SEC-BUTY | .004 | 0.000 | 0.000 | 0.000 | .006 | .003 | .004 | .005 | .006 |
| 1235-TETRAETHYLB | 0.000 | .007 | .046 | .076 | 0.000 | 0.000 | .392 | .519 | .929 |
| 1245-TETRAETHYLB | 0.000 | 0.000 | .024 | .072 | 0.000 | 0.000 | .526 | .698 | 1.356 |
| 1234-TETRAETHYLB | 0.000 | 0.000 | 0.000 | 0.000 | .174 | .351 | .004 | .006 | .010 |
| DIPHENYLMETHANE | 0.000 | 0.000 | 0.000 | 0.000 | 0.000 | .002 | 0.000 | 0.000 | 0.000 |
| UNIDENTIFIED 4 | 0.000 | 0.020 | 0.000 | 0.000 | 0.150 | 0.270 | 0.010 | 0.010 | 0.010 |
| 1,1-DIPHENYLETH | .023 | 0.000 | .008 | .010 | .013 | .019 | .025 | .030 | .047 |
| 1,2-DIPHENYLETHA | 0.000 | 0.000 | 0.000 | 0.000 | 0.000 | 0.000 | 0.000 | 0.000 | 0.000 |
| PENTAETHYLBENZEN | 0.000 | 0.000 | 0.000 | 0.000 | 0.000 | .009 | .016 | .008 | .064 |
| HEXAETHYLBENZENE | 0.000 | 0.000 | 0.000 | 0.000 | 0.000 | 0.000 | 0.000 | 0.000 | 0.000 |
| ETHYLDIPHENYLETH | 0.000 | 0.000 | 0.000 | 0.000 | 0.000 | 0.000 | 0.000 | 0.000 | .012 |
| UNIDENTIFIED 5 | 0.000 | 0.000 | 0.000 | 0.000 | 0.000 | 0.000 | 0.000 | 0.000 | 0.000 |

FIG. 15(continued)

TURBULENT FLOW PROCESS, MONOALKYL AROMATIC PRODUCTION PROCESS AND REACTOR FOR SUCH PROCESS

BACKGROUND OF THE INVENTION

1. Field of the Invention

This invention is directed to a process for the alkylation of aromatic compounds to produce alkyl aromatics; to a reactor useful in such a process; and to processes which affect turbulent intermingling of reactants and a reactor useful in such processes.

2. Description of Related Art

Efficient mass transfer, control of reactant temperature, and co-production of energy at a sufficient level to be useful are several of the problems confronting today's chemical processing art. In many processes, the use of corrosive reactants and catalysts require more durable, stronger apparatuses, often made from expensive corrosion-resistant materials. For example, in various prior art processes for the catalytic alkylation of hydrocarbons, acid catalyst (e.g., hydrofluoric or sulfuric acid or aluminum chloride) is transported through the reaction system and through the recovery system. Apparatuses used in such processes (pumps, vessels, valves, heat exchangers, etc.) are made from expensive alloys. Temperature plays a critical role in such processes and can limit design possibilities.

The production of ethylbenzene by the traditional aluminum chloride ($AlCl_3$) catalyzed reaction of ethylene and benzene has been in commercial use for decades. Ethylbenzene is used in large quantities for the manufacture of styrene monomer, the raw material for polystyrene. Often the catalyst is a liquid, $AlCl_3$ complex. The reaction being carried out in a heterogeneous liquid medium composed of the catalyst complex and a mixture of ethylated benzenes. A two phase liquid product results: (1) the liquid $AlCl_3$ complex (separated and recycled to the alkylator); and (2) a mixture of unreacted benzene and reaction products such as ethylbenzene, diethylbenzene and higher polyethylbenzenes.

The overall reaction can be expressed simply as:

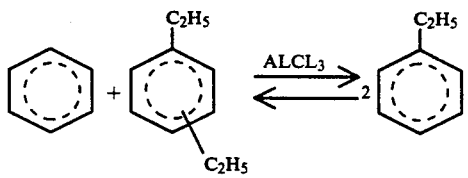

The actual chemistry involved is complex. First, there is the alkylation which involves the reaction of benzene and ethylene to form ethylbenzene as shown above. The alkylation is complicated by the occurrence of minor side reaction such as cracking and polymerization. However, of major importance is the formation of polyethylbenzenes:

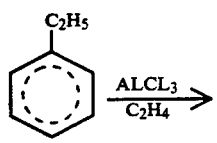

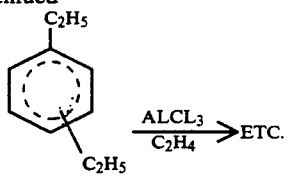

As illustrated by the equation above, the first alkyl group formed activates the aromatic nucleus so that the second alkylation proceeds more readily than the first and so on, at least until steric hindrance intervenes, although hexaethylbenzene is quite readily formed. This results in a mixture of mono, di, tri, and higher ethylbenzenes together with unreacted benzene.

Fortunately, the reaction is reversible, that is reversible in the sense that diethylbenzene, for example, will react under the influence of $AlCl_3$ to form monoethylbenzene:

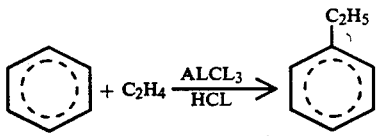

Thus, this transalkylation or reshuffling of ethyl groups among the aromatic rings takes a given reaction mixture to an equilibrium composition that is dependent only on the ratio of ethyl group to benzene rings present. It is these transalkylation reactions that permit virtually all the ethylene and benzene fed to the reactor system to be eventually converted to monoethylbenzene.

In one conventional ethylbenzene process, both the alkylation and transalkylation steps are carried out in a single back-mix reactor using relatively long contact times and low temperatures (30-60 min. and 110°-165° C.). The conventional process also uses relatively high $AlCl_3$ catalyst concentrations. For this reason, the catalyst must be separated from the reaction product and recycled to the reactor. U.S. Pat. No. 3,448,161 teaches the use of short contact times (2 min.) and temperatures up to 250° C. U.S. Pat. No. 3,766,290 discloses the use of catalyst concentrations below the level that requires catalyst recycle. The advantages of separate alkylation and transalkylation reactors are revealed in U.S. Pat. No. 3,848,012. The concept of having separate alkylation and transalkylation steps, but combined in a single piece of equipment is claimed in U.S. Pat. No. 4,179,473. U.S. Pat. No. 3,501,536 teaches the use of a reactor with heat exchange tubes and a plurality of conduits that carry hydrocarbon reactants into a reactor space for intimate mixing and cooling of reactants and catalyst, the reactants entering through a series of spaced openings to the tubes which jet the reactants into an upward spiraling flow around the heat exchange tubes. U.S. Pat. No. 3,817,708 discloses a heat exchanger for use in an alkylation unit in which a heat transfer medium flows through U-tubes while an alkylation catalytic acid flows through the remaining space within a cylindrical shell that houses the U-tubes, the bends in the U-tubes approaching each other near the center of the shell in an adjacent, spaced-apart non-overlapping relationship. All of these processes have certain disadvantages which are overcome by the present invention.

Conventional alkylation reactors consist of open or baffled tanks or towers. These reactors are constructed of brick-lined steel or exotic alloys that resist corrosion by the acid catalyst Tube or coil alkylation reactors have been disclosed in the literature, but have not been commercialized due to a variety of problems.

There has long been a need for an efficient process (and apparatus for such a process) for producing alkyl aromatics. There has long been a need for such a process in which not only is temperature controlled and optimized, but also from which useful heat energy may be efficiently extracted. There has long been a need for such processes and apparatuses permitting relatively high reaction temperatures. There has long been a need for such processes and apparatuses in which pressure is sufficient to maintain aromatic hydrocarbons in liquid phase. There has long been a need for an efficient process and for apparatus useful in it in which reactants are turbulently intermingled.

SUMMARY OF THE PRESENT INVENTION

The present invention, in one embodiment, teaches a process for producing monoalkyl aromatics by the reaction of olefinic and aromatic compounds and takes advantage of the fundamental chemistries of the two major reaction steps, alkylation and transalkylation, to improve the efficiency of known alkyl aromatic production processes. Further, while the improved process of the present invention can be readily applied to new production facilities, it is also applicable to retrofitting into and increasing the efficiency of existing plants.

The present invention teaches a turbulent flow alkylator reactor with reaction heat recovery. In one embodiment of a reactor according to the present invention in which the reaction takes place in reaction tubes within the reactor, each of two reactor heads allow for gaseous reactants to be injected into a liquid stream at the start of each pass through a reaction tube. One or more reaction tubes can be included in any particular pass through the reactor and any desired number of passes may be employed. All tubes of a given pass can be fed with gas from a common gas chamber, and a separate gas chamber can be used for each pass of the reactor. Gas flows from the gas chambers, through gas spargers, and into the reaction tubes where it turbulently contacts the liquid stream.

For each tube of a given pass, one gas sparger protrudes axially down into the tube for a short distance. This configuration allows each tube of a given pass to be individually fed with gas.

The entire liquid feed stream enters the reactor at the start of the first pass. The ends of the reaction tubes open into liquid chambers. There is a liquid chamber at the start of the first pass, one between each two passes, and one at the end of the final pass. As the liquid stream makes its way through the reactor, gas is sparged into the liquid within a reactor tube at the start of each pass.

With such a reactor, residence times are minimized and a uniform distribution of precise amounts of reactants to each tube is made possible. Also, there is easy access to internal parts for cleaning and maintenance. This reactor allows relatively fast and highly exothermic alkylation reactions to be carried out in a manner such that the heat of reaction is used directly to drive an ethylbenzene finishing train or to heat other streams in a process.

In one embodiment the reactor is of multi-pass, tube-in-shell design with ethylbenzene finishing tower bottoms applied to the shell as a heat transfer medium and an alkylation carried out in the tubes. Thus, the reactor shell serves as a tower reboiler. It is preferred that linear velocities inside the tubes are such that the reactor operates near the plug-flow region. A plurality of ethylene injectors help to control the reaction exotherm. Contact times of less than one minute are possible.

In certain embodiments of the present invention processes are employed which utilize apparatuses which provide for a uniform feeding of liquid reactants to a plurality of reaction tubes of a particular pass through the reactor. This is accomplished by adjusting flow and design parameters including sparger disposition, dimensions, and reaction tube disposition and dimensions.

In preferred embodiments, reaction temperatures greater than 200° C. are achieved and reaction pressures are sufficient to maintain aromatic hydrocarbons in the liquid phase. Although reactors according to this invention are particularly suited to alkylation processes such as ethylbenzene production, they may be used for producing a variety of valuable chemicals which involve reacting a gas with or in the presence of a liquid in specific molar or weight ratios and are particularly valuable for highly exothermic gas-liquid reaction systems that are advantageously carried out at elevated temperatures and/or pressures, such as the following reactions: the production of cumene by reacting propylene with benzene; the production of ethyltoluene by reacting ethylene and toluene; the alkylation of an alkene onto an aromatic compound. Processes according to the present invention are also useful in reactions involving two liquid reactants, such as, but not limited to, polymerization reactions and reactions of two liquid reactants in which different materials are added in precise amounts at precise points in the process apparatus.

The processes and apparatuses taught by the present invention include, but are not limited to, processes involving only liquid reactants; only gas reactants; or are endothermic reactions.

Certain embodiments of a process and apparatus according to the present invention have the following features:

High efficiency recovery of reaction heat to directly drive an ethylbenzene finishing train. Conventional processes, at best, raise low-grade steam with a portion of reaction heat.

Reduction of by-product and heavy residue formation (i.e. increasing yield) by conducting alkylation and transalkylation steps under optimum conditions, allowing optimization of each process and maximization of yield of each process as well as increasing catalyst efficiency. Various conventional processes carry out both reaction steps at the same temperature and catalyst concentration.

Short contact time (residence time in reaction tubes) and high turbulence in alkylation reduce or eliminate plugging and fouling.

Reduction of ethylene polymerization (e.g., tar) by providing optimum mixing of reactants.

Polyethylbenzenes are not recycled to the alkylator thereby increasing yield and reducing the amount of transalkylation required.

As the reactor approaches plug-flow, alkylation kinetics improve monoethylbenzene selectivity.

Precise control of the alkylation reaction exotherm result in improved yields and reduced solid formation (fouling and plugging).

High turbulence on the alkylator tube side and boiling on the shell side result in uniform, extremely high heat transfer efficiency thereby minimizing the cost of special alloy equipment.

Multiple injections of one or more reactants along the path of the reactor reduce or eliminate uncontrolled exotherms and result in much more isothermal operation.

Uniform distribution of precise amounts of gaseous and liquid reactants to each tube helps control reactant ratios and optimizes product distributions. While reducing liquid or gas maldistribution (non equal amounts of liquid or gas flowing into various tubes of a given pass).

Reactor size is reduced or minimized due to higher operating temperatures, turbulent mixing of the reactants, high heat transfer rates, and increased reaction rates.

It is, therefore, an object of the present invention to provide processes for the new, useful, efficient, and non-obvious production of monoalkyl aromatic compounds.

Another object of the present invention is the provision of apparatuses for use in such processes which apparatuses are new, useful, efficient and non-obvious.

A further object of the present invention is the provision of new, useful, efficient and non-obvious processes for reacting a gas or a liquid in the presence of a liquid, particularly highly exothermic gas-liquid reactions carried out at elevated temperatures and/or pressures.

An additional object of the present invention is the provision of new, useful, efficient and non-obvious apparatuses for such processes.

A further object of the present invention is the provision of efficient processes and apparatus useful in such processes for the turbulent intermingling of reactants.

The present invention recognizes and addresses the previously-mentioned long-felt needs and provides a satisfactory meeting of those needs in its various possible embodiments. To one of skill in this art who has the benefits of this invention's teachings and disclosures, further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions or further improvements.

BRIEF DESCRIPTION OF THE DRAWINGS

So that the manner in which the above-recited features, advantages and objects of the invention, as well as other which will become clear, are attained and can be understood in detail, more particular descriptions of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

FIGS. 11, 11a and 12 present data from a run of a single tube reactor according to the present invention.

FIG. 14 presents data from a process according to the present invention.

FIG. 15 presents data from a process according to the present invention.

DETAILED DESCRIPTION OF THE DRAWING

Figure 1:
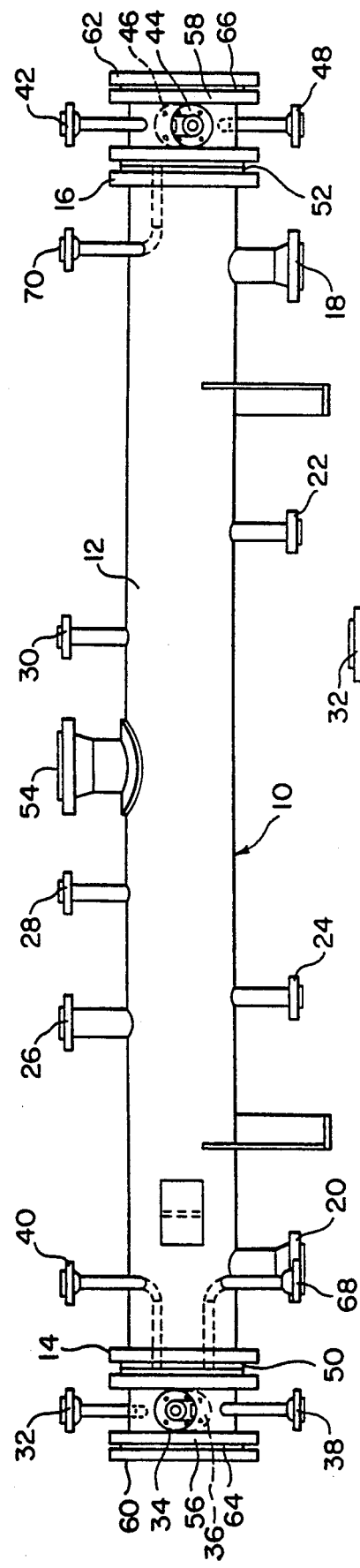
FIG. 1 is a schematic view of a reactor system according to the present invention.
Figure 2:
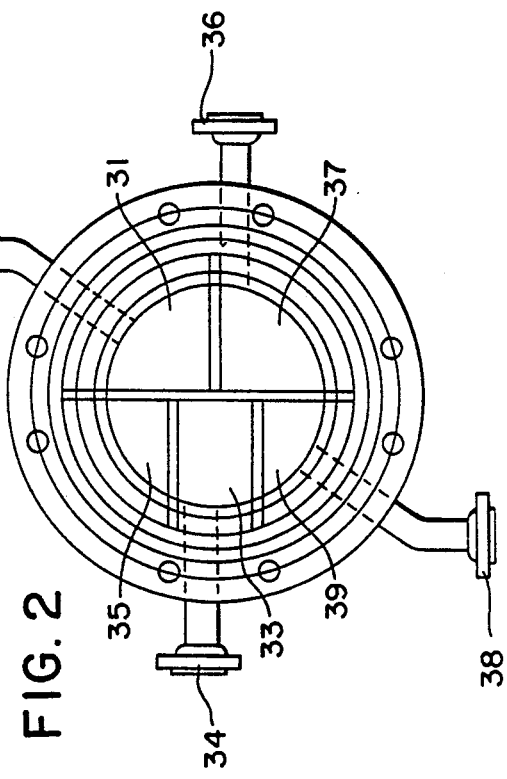
FIG. 2 is an end view of the reactor system of FIG. 1.

Referring now to FIGS. 1 and 2, a reactor system 10 according to the present invention has a shell section 12, a head 56 on a left end 14, and a head 58 on a right end 16. The shell section 12 (made e.g. from carbon steel) has a variety of inlets and outlets including: reactant entry nozzle 68; heat transfer medium inlet nozzles 18 and 20; drains 22 and 24; a relief outlet 26; instrument access nozzles 28 and 30; ethylene feed inlet for the head 56—inlets 32, 34, 36 and 38; ethylene feed inlets for the head 58–42, 44, 46 and 48; a product discharge outlet 40; and a tube side relief outlet 70; and a heat transfer medium outlet 54.

A primary tube sheet 50 made from Hastelloy B-2 (TM) material or a multi-layer member made from layers of carbon steel, nickel, and Hastelloy B-2 explosion bonded or welded together; e.g. ⅜ inch Hastelloy B-2, ⅛ inch nickel, and 7 to 9 inches of carbon steel is disposed between the shell section 12 and the head 56. A primary tube sheet 52 is disposed between the shell section 12 and the head 58. End plates close off each head. An end plate 60 with a sealing gasket 64 is secured to the head 58. It is preferred that whatever in the reactor encounters the reactants is made from Hastelloy B-2 (TM) material.

As shown in FIG. 2, each ethylene feed inlet 32, 34, 36, 38 feeds into a particular section of the reactor system 10. The reactor system 10 has eight sets of transverse reaction tubes (not shown). Each set of tubes is fed by an individual ethylene feed; hence: there are eight such inlets 32, 34, 36, 38 and 42, 44, 46, 48. At the initial end of each set of reaction tubes, ethylene is fed into the tubes by feeding ethylene into a chamber and from it into spargers extending into each reaction tube from the chamber. Ethylene and other reactants (benzene and catalyst complex) move through the tubes, reacting and producing heat and reaction products. At the other end of the tubes, the tubes end in another liquid chamber from which extends another set of reaction tubes. Ethylene is again injected by spargers into the beginning of the new set of reaction tubes and the added ethylene, reactants, and products move back in the other direction through the shell section with the reaction proceeding as the materials move through the tubes. In the reactor system 10 of FIGS. 1 and 2, the materials make eight passes through the shell section; hence there are eight ethylene feeds.

Ethylene feed 38 at a first end of the reactor as shown in FIG. 2 feeds ethylene into an ethylene chamber 39 from which it is fed via spargers (not shown) to a first set or pass of reaction tubes (not shown) containing benzene and catalyst complex. After these materials move across the shell section 12 in the first pass through the first set of reaction tubes, additional ethylene is injected via ethylene feed 48 at the other end (a second end) of the reactor which feeds into another ethylene chamber (not shown). From this chamber ethylene flows through spargers (not shown) into the second set or pass of reaction tubes (not shown) which extend to and intercommunicate with liquid chamber 37 (FIG. 2). Via ethylene feed nozzle 36, additional ethylene is injected into a third set of reaction tubes which extend from chamber 37 to the second end of the reactor to another chamber (not shown). A fourth set of reaction tubes extending from this chamber are fed with ethylene from ethylene feed nozzle 46 (via spargers) and the tubes extend back to a chamber 33. A fifth set of reaction tubes (not shown) extending from the chamber 33 are fed with ethylene from an ethylene feed nozzle 34, the ethylene entering the tubes through spargers (not shown). These tubes (the fifth, set) extend to a chamber (not shown) at the second end, of the reactor. The next set of tubes (the sixth set) extending from this chamber are fed with ethylene from ethylene feed nozzle 44 (via spargers). These tubes (the sixth set) extend to the first end of the reactor and end in a chamber 31. Additional ethylene is injected into spargers (not shown) disposed in a seventh set of reaction tubes (not shown) via ethylene feed nozzle 32 and spargers (not shown). The seventh set of reaction tubes extend from the chamber 31 in the first end of the reactor to another chamber (not shown) from which the eighth and final set of reaction tubes extends. Ethylene is fed via an ethylene feed nozzle 42 through spargers (not shown) into the final (eighth) set of reaction tubes. The eighth set of reaction tubes extend from the chamber adjacent ethylene feed nozzle 42 in the second end of the reactor to a chamber 35 (FIG. 2) from which products of the reaction exit the reactor via product outlet 40.

Figure 3:
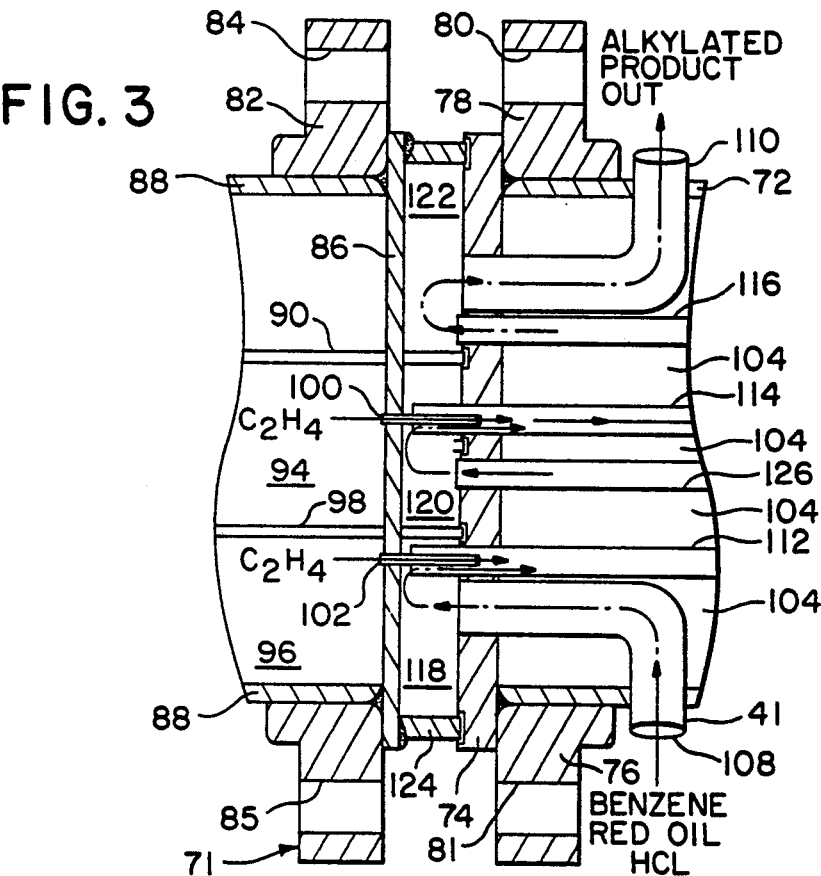
FIG. 3 is a cross-sectional schematic view of a portion of a reactor system according to the present invention.

Shown schematically in FIG. 3 is a four pass reactor system 71 according to the present invention having four sets or passes of reaction tubes, with tubes 112, 126, 114, 116 (shown). A head 76 is secured to a shell section 72 by securing a flange 78 of the shell section 72 to a flange 82 of the head 76 by bolts (not shown) extending through bolt holes 84, 85 (in flange 82) and bolt holes 80, 81 (in flange 76).

A secondary tube sheet 86, a gas chamber channel wall 88, and gas chamber inner walls 90 and 98 (made e.g. from Hastelloy B-2 (TM) alloy and welded together) define two ethylene gas chambers 94 and 96 each fed by an ethylene feed nozzle (not shown, like feed 32–38, 42–48). Ethylene is conveyed from the ethylene gas chambers 94 and 96 by sparger feed tubes 100 and 102, respectively, which extend into reaction tubes 114 and 112, respectively. The secondary tube sheet 86 is spaced apart from a primary tube sheet 74 by a benzene chamber channel wall 124 which (with extensions of the gas chamber inner walls 90 and 98 extending through the secondary tube sheet 86 to contact the primary tube sheet 74) define reactant entry chambers 118 and liquid chambers 120 and 122.

Reactants, e.g. liquid benzene and a catalyst complex, flow through a reactant inlet nozzle 108 extending through the shell section 72 and through the primary tube sheet 74, into the reactant entry chamber 118 at a first end of the shell section 72. From this chamber 118, the reactants flow into the reaction tube 112 in which they turbulently encounter ethylene gas fed into the reaction tube 112 through the sparger tube 102. These materials then flow turbulently through the reaction tube 112 to the other end (a second end not shown) of the shell section 72, ending in another reactant entry chamber (not shown) from which another reaction tube 126 extends back to the head 76 in the first end of the shell section. Before the materials leave the second end of the shell section, additional ethylene is injected into reaction tube 126 and the reactants then flow through reaction tube 126 to the liquid chamber 120. Thus the reactions proceed with materials moving from the chamber 120; into and through reaction tube 114; into another chamber (not shown) at the other end of the shell section; into reaction tube 116; into chamber 122; and out through product outlet nozzle 110. Through an ethylene sparger 100, ethylene from an ethylene chamber 94 is injected into reaction tube 114. Similarly at the other (second) end of the reactor, ethylene is sparged into the reaction tube 116. Although only four reaction tubes are shown in FIG. 3, a schematic drawing, a plurality of reaction tubes can extend from each of the chambers, 118, 120 and 122.

The reaction tubes within shell section 72 are surrounded by a heat transfer medium 104 (e.g. but not limited to liquid polyethylated benzene or water) to which is transferred the heat of the ethylene-benzene reaction. Via heat transfer medium inlet and outlet nozzles (not shown; like nozzles 18, 20, and 54 in FIG. 1) the heat transfer medium circulates due to a thermosiphon effect or by the action of a conventional pump and thus the heat exchange medium 104 is moved through the shell section 72. The heat is extractable and can be used, e.g. to heat a stream in the process; to provide heat for the distillation of the various products present in the product stream flowing from the outlet nozzle 110; or to generate steam for other uses.

Figure 4:
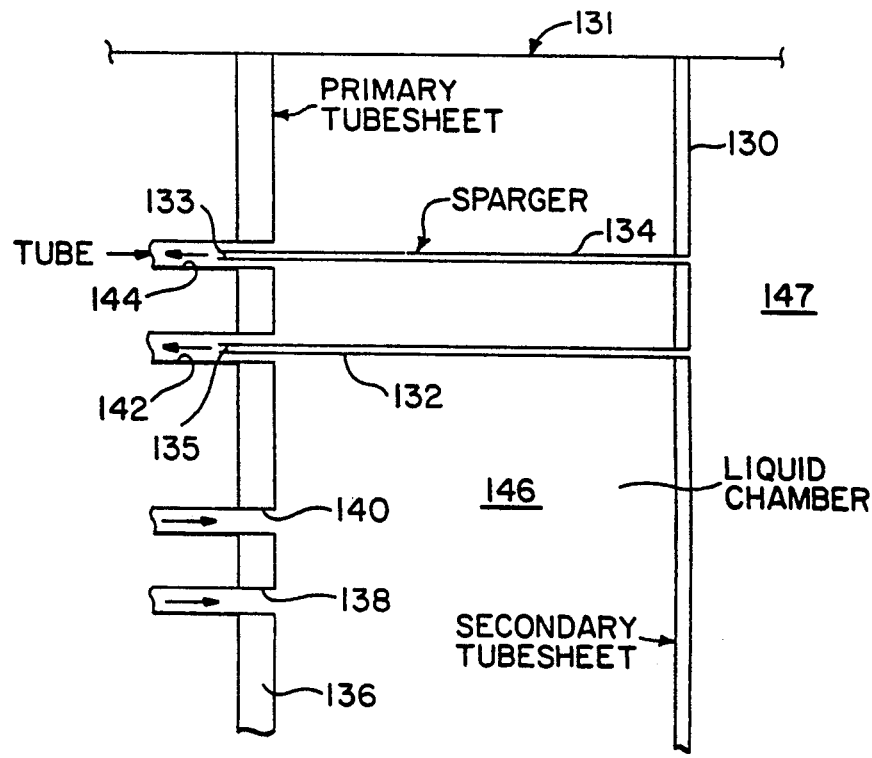
FIG. 4 is a schematic view of a portion of a reactor system according to the present invention.

As shown in FIG. 4, a reactor system 131 (partially shown) similar to reactor systems 10 and 71, may employ sparger tubes 132 and 134 that extend into reaction tubes 142 and 144 that are flush with, but do not extend beyond, a primary tube sheet 136. The spargers extend from a secondary tube sheet 130 on the other side of which (left side in FIG. 4) is an ethylene gas chamber 147 like, e.g. the chamber 96 in the reactor system 71 shown in FIG. 3. The sparger tubes 132 and 134 extend across a liquid reactant chamber 146 from which reactants flow into the reaction tubes 142 and 144.

There are three pressure drops in an apparatus such as the reactor system 131 which affect material distribution—the pressure drop $P_1$ from the liquid chamber 146 to the interior of the reactor tubes 142 and 144; the pressure drop $P_2$ across the liquid chamber 146, i.e. the pressure drop across the spargers 132 and 134; and the ethylene pressure drop $P_3$ at the exit holes 133 and 135 in the ethylene spargers. To maximize the uniformity of the amount of liquid flowing down each reactor tube, pressure drop $P_1$ should be significantly greater than pressure drop $P_2$. In other words, the opening of the reactor tube 142 should experience liquid at almost the same pressure as the pressure of liquid at the opening to the reactor tube 144. For example, if the liquid pressure at the opening to the reactor tube 142 is 370 p.s.i. and $P_1$ is 3 p.s.i., the pressure of the liquid at the opening to the reaction tube 144 should not be significantly less than 370 p.s.i. (it is preferred that it be at least about 369.7 p.s.i.). Similarly, the pressure drop $P_3$ at the holes 133 and 135 in the ethylene spargers 134 and 132, respectively, should be significantly greater than a pressure drop $P_4$ across the ethylene chamber 147. In other words, the effect of ethylene exiting sparger 134 should not be so great that it significantly reduces the pressure of ethylene experienced at the opening to the sparger 132. Liquid flows into the chamber 146 through reaction tubes 138, 140.

Figure 5A:
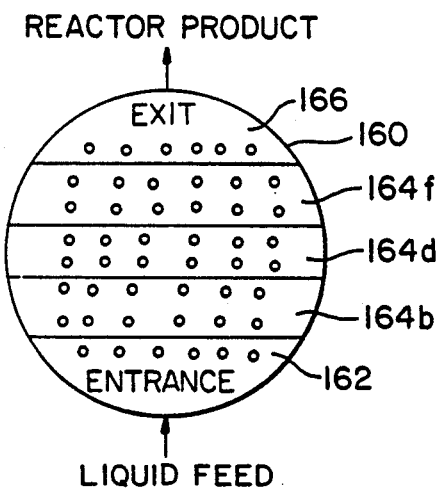
FIGS. 5a and 5b are schematic end views of a reactor system according to the present invention.
Figure 5B:
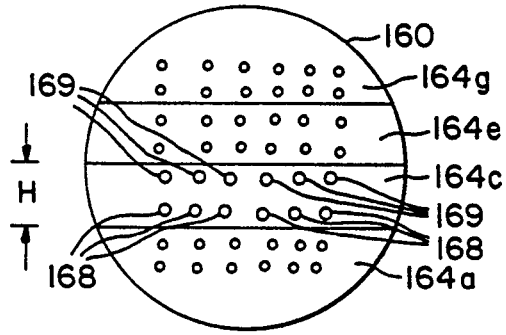
Figure 6A:
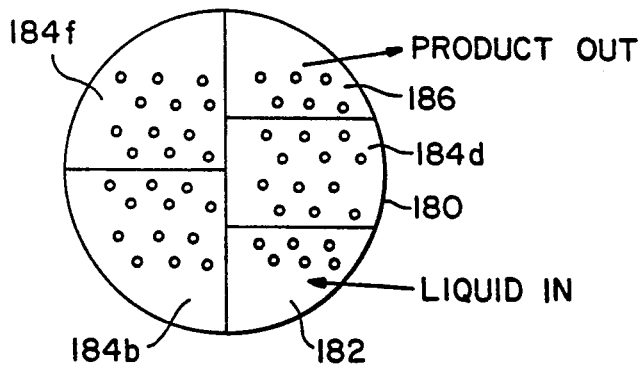
FIGS. 6a and 6b are schematic end views of a reactor system according to the present invention.
Figure 6B:
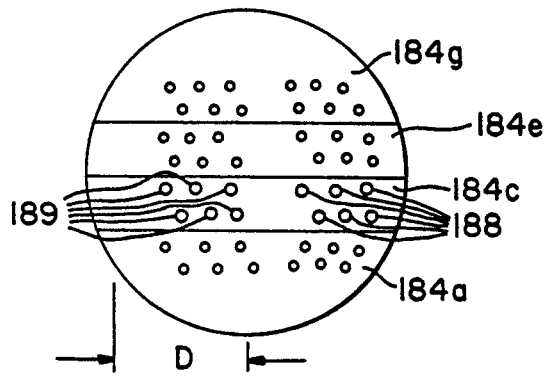

FIGS. 5a, 5b, 6a and 6b show two different chamber arrangements for reactors according to the present invention. FIGS. 5a and 5b show a "ribbon" chamber arrangement in which ethylene gas chambers and reactant chambers extend from one side of the head to the other; a plurality of reaction tubes intercommunicate with the reactant chambers; and a plurality of sparger tubes extend across the reactant (liquid) chambers. FIGS. 6a and 6b show a "quadrant" chamber arrangement (as in FIG. 2). The chamber arrangement refers to the way in which partitions (made e.g. from Hastelloy B-2 (TM) material) in the heads are oriented, and consequently affects the liquid flow geometry through the heads. A ribbon chamber arrangement (FIGS. 5a, 5b) is superior to a quadrant chamber arrangement (FIGS. 6a, 6b) for two reasons. Both reasons are related to the inherent lower liquid chamber crossflow velocities in the ribbon layout relative to that in the quadrant layout. First, lower crossflow velocities reduce or prevent vibration of the unsupported spargers which extend into the head. Second, lower crossflow velocities result in a lower liquid chamber crossflow pressure drop ($P_2$). A lower crossflow pressure drop results in improved liquid flow distribution to the reaction tubes, resulting in improved yields. The advantages of the chamber arrangement become more significant as the scale of the reactor increases.

As shown in FIGS. 5a and 5b, a ribbon arrangement, each section of a reactor shell 160 represents a reactant entry chamber 162 (like chamber 118, FIG. 3); liquid chambers 164 a-g (like chamber 120, FIG. 3); or a chamber 166 from which product exits (like chamber 122, FIG. 3). Eight reaction passes of reactants take place in the shell 160; i.e. passes between sections:
1. 162 to 164a
2. 164a to 164b
3. 164b to 164c
4. 164c to 164d
5. 164d to 164e
6. 164e to 164f
7. 164f to 164g
8. 164g to 166.

As in the systems of FIGS. 1 and 3, ethylene is injected into reaction tubes on each reaction pass.

In each of the sections of the shell 160, reaction tubes are arranged as the tubes 168 and 169 shown in section 164c. Reactants enter section 164c (a liquid chamber) through the reaction tubes 168 and leave the section through the tubes 169. The height of the section 164c is H and the reactants from the tubes 168 must traverse the majority of the height H to enter the tubes 169. As shown there are six tubes 168 and six tubes 169, but it should be understood that this invention is applicable to systems with one tube and systems with more than one tube, e.g. five hundred tubes or more.

As shown in FIGS. 6a and 6b, a quadrant arrangement, a reactor shell 180 is also divided into chambers or sections, a reactant entry chamber 182; liquid chambers 184a-g; and a product exit chamber 186. Again, as in the system of FIGS. 5a and 5b, there are eight reaction passes:
1. 182 to 184a
2. 184a to 184b
3. 184b to 184c
4. 184c to 184d
5. 184d to 184e
6. 184e to 184f
7. 184f to 184g
8. 184g to 186.

This chamber arrangement is like that of the system of FIGS. 1 and 2. Focusing on chamber 184c and comparing it to chamber 164c of the system of FIGS. 5a and 5b, it is apparent that part of the reactants flowing into chamber 184c from a set of reaction tubes 188 and across the chamber 184c to another set of reaction tubes 189 traverses a greater distance D than the height H of the chamber 164c. Because of this difference in the length of the flow path and the difference in the relative dispositions of the sets of tubes it is more difficult to achieve uniform flow distribution in the tubes 189 than in the tubes 169. Crossflow velocities of reactants in the shell 160 are lower than those in the shell 180. The small unnumbered circles in FIGS. 5a, 5b, 6a and 6b represent reaction tubes.

In preferred embodiments of reactor systems according to the present invention there are a number of critical design parameters. The discussion of these parameters that follows is with respect to a 1,500 million pound/year system for ethylbenzene production according to the present invention.

Liquid Chamber Width—The liquid chamber width is defined as the inside distance between the primary and secondary tubesheets (e.g. between sheets 74 and 86 in FIG. 3) In preferred embodiments, the liquid chamber width is critical to achieving uniform liquid flow distribution among all tubes of a given pass. One key to improving uniform liquid flow distribution is to increase the ratio of the pressure drop of the liquid entering the tubes to the pressure drop of the liquid flowing across the extended gas spargers. It is preferred that this pressure drop ratio, e.g., $P_1/P_2$ FIG. 4 be greater than 10, but most preferably equal to or greater than 25 to reduce liquid maldistribution to less than 15% and most preferably less than 3.5%. In terms of the pressure drops $P_1$ and $P_2$ discussed in relation to the system of FIG. 4, the ratio $P_1/P_2$ should be preferably greater than 10 and most preferably greater than 25.

An increase in the liquid chamber width results in an increase in the pressure drop ratio. For the following conditions:
76" I.D. liquid channel, (heads and shell section)
8 pass reactor,
Ribbon pass arrangement,
0.750" 18 BWG reaction tubes,
500 tubes/pass,
1.25 pitch ratio, 30° layout,
0.375" O.D. gas spargers, Liquid Benzene+Catalyst feedrate=400,000 lb/hr,
Liquid density=37.5 lb/ft$^3$,
Liquid viscosity=0.14 cp, the liquid chamber width should be at least 4″ (resulting in a pressure drop ratio of 20) to reduce liquid maldistribution to less than 3.5%. Because the pressure drop ratio is not a function of total liquid flowrate, liquid flow distribution and the choice of a suitable liquid chamber width are not affected by reactor capacity.

"Pitch ratio" and layout refers to the disposition of and spacing between reaction tubes. Reaction tubes in a triangular layout result in a higher heat transfer coefficient than tubes in a square layout, and also require a smaller diameter shell for a given number of tubes. In a squared layout one tube may mask flow to or around another tube. It is preferred that tubes be offset from each other. "Pitch" is the distance between two tubes. "Pitch ratio" is the ratio of pitch to the outside diameter of the tubes —A "30°" layout" refers to equiangularly spaced tubes in a generally triangular array; i.e. connecting three adjacent tubes forms a triangle with one tube at the top and two on the base, a line drawn from the top tube to the base bisects the top angle of the triangle, i.e. forming two 30° angles.

Sparger diameter—In preferred embodiments, the ethylene sparger tube outer diameter is critical to achieving uniform liquid flow distribution among all tubes of a given pass. As the sparger outer diameter increases for a given reaction tube inner diameter, the pressure drop of the liquid entering a reaction tube increases. The ratio of this pressure drop to the pressure drop of the liquid flowing across the extended gas spargers increases, and liquid flow distribution improves. However, as the sparger outer diameter increases, the overall pressure drop through the reactor increases as well as $P_1$. For the previously listed operating conditions, a sparger, tube outer diameter of at least ⅜″ reduces liquid maldistribution to less than 3.5%. It is preferred that this diameter in combination with other design factor be such that e.g. in the system of FIG. 4 $P_1$ be significantly greater than $P_2$, i.e. greater than 10 and preferably greater than 25.

Sparger hole size—the sparger hole is the opening at the end of the sparger tube through which gas (or liquid in other processes) flows into the reaction tube (e.g. holes 133, 135, FIG. 4). In preferred embodiments, the sparger hole size is critical to achieving uniform gas flow distribution among all tubes of a given pass. As the sparger hole diameter decreases, gas flow distribution improves. For a total ethylene feedrate of 54,000 lb/hr and the reactor configuration described previously, a sparger hole diameter of 0.0625″ limits gas flow maldistribution to less than 2%. It is preferred that sparger hole size be adjusted so that gas flow maldistribution is at least less then 15%.

Reaction Tube diameter, Reaction Tube length, Number of passes, and Number of reaction tubes per pass —The reactor configuration parameters of tube diameter, tube length, number of passes, and number of tubes per pass can be optimized simultaneously. Four criteria considered in optimizing preferred embodiments of this invention are: minimizing residence time in the reactor; maintaining a recommended heat transfer flux across the tubes and maximizing heat recovery; and ensuring maximum or complete reaction of ethylene. For the following conditions:
Ethylene feedrate=54,000 pounds/hr,
Benzene feedrate=400,000 pounds/hr,
Ethylene inlet temperature=50° C.,
Benzene inlet temperature=220° C.,
Reactor pressure at inlet=395 psia,
Shellside boiling temperature (vaporization begins) =208° C.,
Shellside exit vapor fraction (% vapor of exiting heat transfer medium)=0.200, optimum values for tube length and number of tubes per pass are 23 feet and 500, respectively. Tube diameter is held to a minimum of 0.75″ O.D., and the number of passes was held at a maximum of 8. A preferred heat transfer flux is between 2000 and 8000 Btu/hour/square foot of heat transfer surface area. For this embodiment it is about 4000 Btu/hr/ft$^2$. Sparger Tube penetration length—The sparger penetration length is defined as the axial distance that an ethylene sparger protrudes down into the start of a reaction tube. In preferred embodiments, the sparger penetration length should be no less than ⅛″ to ensure that no ethylene backs out of a reaction tube. The sparger penetration length accounts for only about 10% of the total pressure drop of the liquid tube-entry pressure drop, and so plays only a minor role in determining liquid flow distribution and total pressure drop through the reactor.

Figure 13:
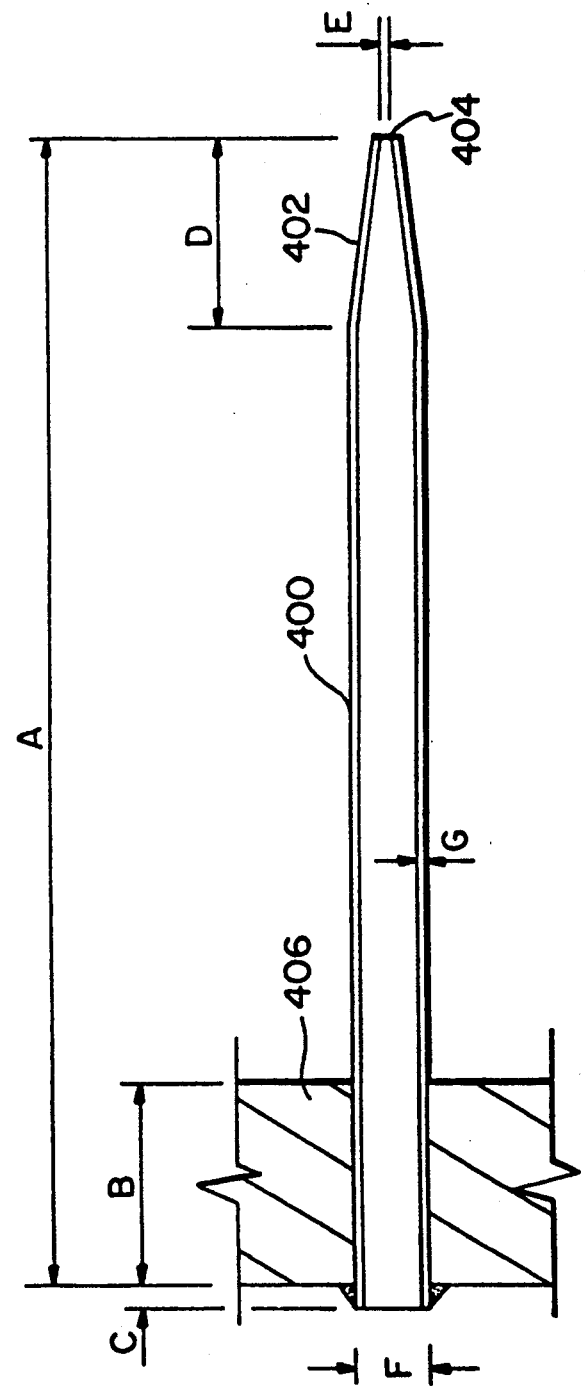
FIG. 13 is a cross-sectional view of a gas sparger used in reactors according to the present invention.

As shown in FIG. 13 an ethylene gas sparger 400 according to the present invention, made from a piece of Hastelloy B-2 (TM) material tubing, has a nozzle end 402 which is swaged down so that a hole 404 of desired size provides an exit opening for ethylene gas to flow into a reaction tube. The sparger 400 is shown as welded to a tube sheet 406 of a thickness B. The sparger's overall length is A, the length of the nozzle end is D, the sparger tube outer diameter is F, side wall thickness is G, the hole opening size is E, and the sparger extends a length C beyond the tube sheet for ease of welding. In one preferred embodiment these dimensions are:

A=7 inches
B=1 inch
C=one eighth inch
D=one half inch
E=0.063±0.002 inches
F=three eighths inch
G=0.065 inches It is within the scope of this invention to have more than one ethylene feed nozzle feeding into a single ethylene chamber and, in one preferred embodiment, two ethylene feed nozzles feed each ethylene chamber producing a more uniform feed to the gas spargers. Also, liquid distribution may be more uniform with a plurality of product outlets rather than one and, in one preferred embodiment four product outlets communicating with a single chamber are employed. Similarly, liquid distribution to the reaction tubes of a particular chamber may be more uniform with a plurality of liquid inlets into the chamber and, in one preferred embodiment, four liquid inlets feed into a single liquid (benzene and catalyst) chamber.

Figure 7:
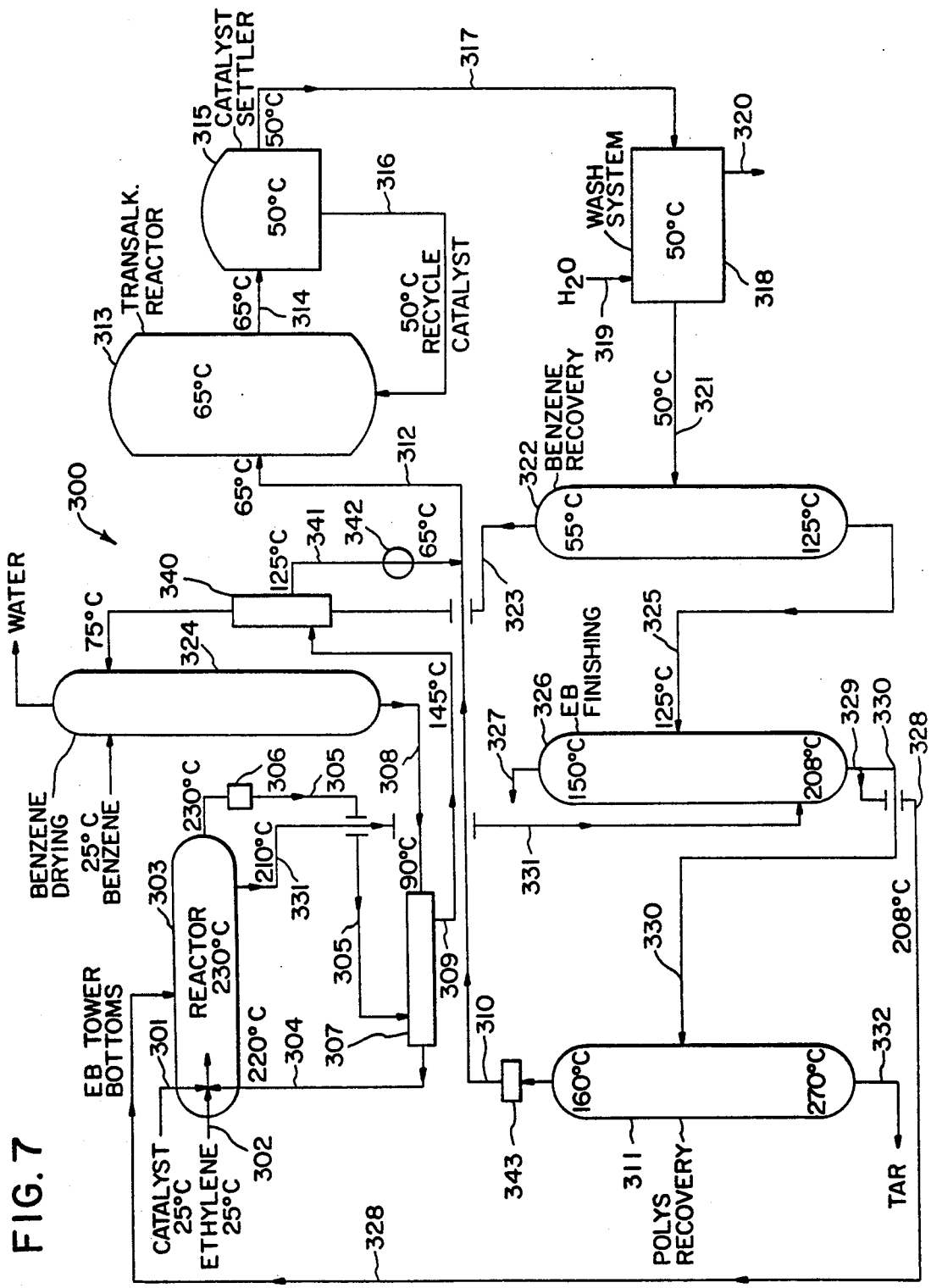
FIG. 7 is a schematic view of a process according to the present invention.

FIG. 7 illustrates schematically a process 300 for producing ethylbenzene according to the present invention. Via a feed line 301, catalyst (about 400 pounds per hour at about 25° C.), such as aluminum-chloride—HCL catalyst for this reaction, is fed into an end head (not shown; like head 56, FIG. 1 or head 76, FIG. 3) of a reactor 303 via /a feed line 302. Via a feed line 302 ethylene gas at about 25° C. is fed into the head of the reactor 303. Via a feed line 304 benzene at about 220° C. is fed into the reactor 303. It is preferred that an excess of benzene at least 100%, but preferably 200% or more (e.g. 3 molecules of benzene for each molecule of ethylene) be fed to the reactor. The reactor 303 is like the previously described reactors according to the present invention.

Reaction products and other materials (ethylbenzene, polyethylated benzenes, benzene, catalyst) exit from the reactor 303 via line 305 at about 230° C. A valve 306 in line 305 controls the pressure in the reactor 303 (set, e.g. at about 350 p.s.i.g.). The materials in line 305 are relatively hot (230° C. in this example) and they are fed through a heat exchanger 307 in heat transfer relationship with benzene at 90° C. from a line 308. This benzene is heated from 90° C. to 220° C. (line 304). The reaction products and materials (now cooled to 145° C.) flow from the heat exchanger 307 in line 309. Via line 309 this stream then flows to a heat exchanger 340 wherein heat is transferred from the materials in line 309 to a stream 323 (primarily benzene) from a benzene recovery tower 322. The materials from line 309 exit the heat exchanger in line 341 at about 125° C. Prior to joining materials in line 310, the materials in line 341 are cooled by a cooler (e.g. fan) 342 to about 65° C.

In line 312 the reaction products and other materials in line 341 mix with polyethylated benzenes recovered by a tower 311 and flow through line 312 to a transalkylation reactor 313. The transalkylation reactor 313 is operated at 65° C. It produces a product line 314 in which the amount of polyethylated benzenes from line 312 have been reduced and the amount of ethylbenzenes has been increased. Line 314 also contains unreacted catalyst.

The materials in line 314 are fed to a catalyst settler 315 run at, e.g., 50° C. It produces: recyclable catalyst which can be fed back to the transalkylation reactor 313 via a line 316 (at 50° C.); and a materials stream which exits the settler 315 via a line 317. Line 317 contains ethylbenzene, benzene, polyethylated benzenes, and catalyst. It is fed to a wash system into which water is fed via a line 319 and from which water and dead catalyst exit via a line 320.

The materials exiting from the wash system 318 flow via a line 321 (at 50° C.) to the benzene recovery tower 322. The material stream in line 321 is, e.g., about 53% benzene, about 40% ethylbenzene, and about 7% polyethylated benzenes. Benzene exits from the top of this distillation tower and flows via a line 323 to a benzene drying tower 324. The materials remaining from line 321 (ethylbenzene and polyethylated benzenes) flow via a line 325 at 125° C. to an ethylbenzene finishing distillation tower 326. Ethylbenzene at 150° C. exits from the top of the tower 326 via a line 327. Polyethylated benzenes exit the tower 326 via a line 329. A portion of them (e.g. about 1%) flow via a line 330 to the polyethylated benzenes recovery distillation tower 311. Another portion of the polyethylated benzenes at 208° C. are flowed via a line 328 to act as the heat transfer medium in the reactor 303 ("EB TOWER BOTTOMS"). These polyethylated benzenes are heated in the reactor 303 by the exotherm from the ethylene—benzene reaction in the reactor's reaction tubes. The heated polyethylated benzenes at, e.g., about 210° C. flow from the reactor 303 via a line 331 back to the ethylbenzene finishing tower 326 to provide heat energy for the tower 326. The EB TOWER BOTTOMS in line 328 are essentially 100% liquid. A vapor/liquid combination exits the reactor 303 via line 331 and it is preferred that it be about 5% to about 50% vapor, most preferably about 15% vapor and about 85% liquid.

The reaction products and other materials in line 312 may be present as follows (% by weight): 60% benzene; 30% ethyl benzene; 10% polyethylated benzenes; negligible amount of catalyst. The benzene content might range as low as 30%; the ethylbenzenes as low as 5% and as high as 45%; and the polyethylbenzenes as high as 30%. The stream in line 314 is preferably: about 53% benzene; about 40% ethylbenzene; and about 7% polyethylated benzenes—all ranging as dependent on the ranges stated regarding line 312. From the polyethylated benzenes recovery tower 311 polyethylated benzenes exit via a line 310 and proceed to join with the products from the reactor 303 (in line 309) to flow to the transalkylation reactor 313. A condenser 343 cools the materials in line 310. Tar (residue) flows from the tower 311 via a line 332.

Figure 8:
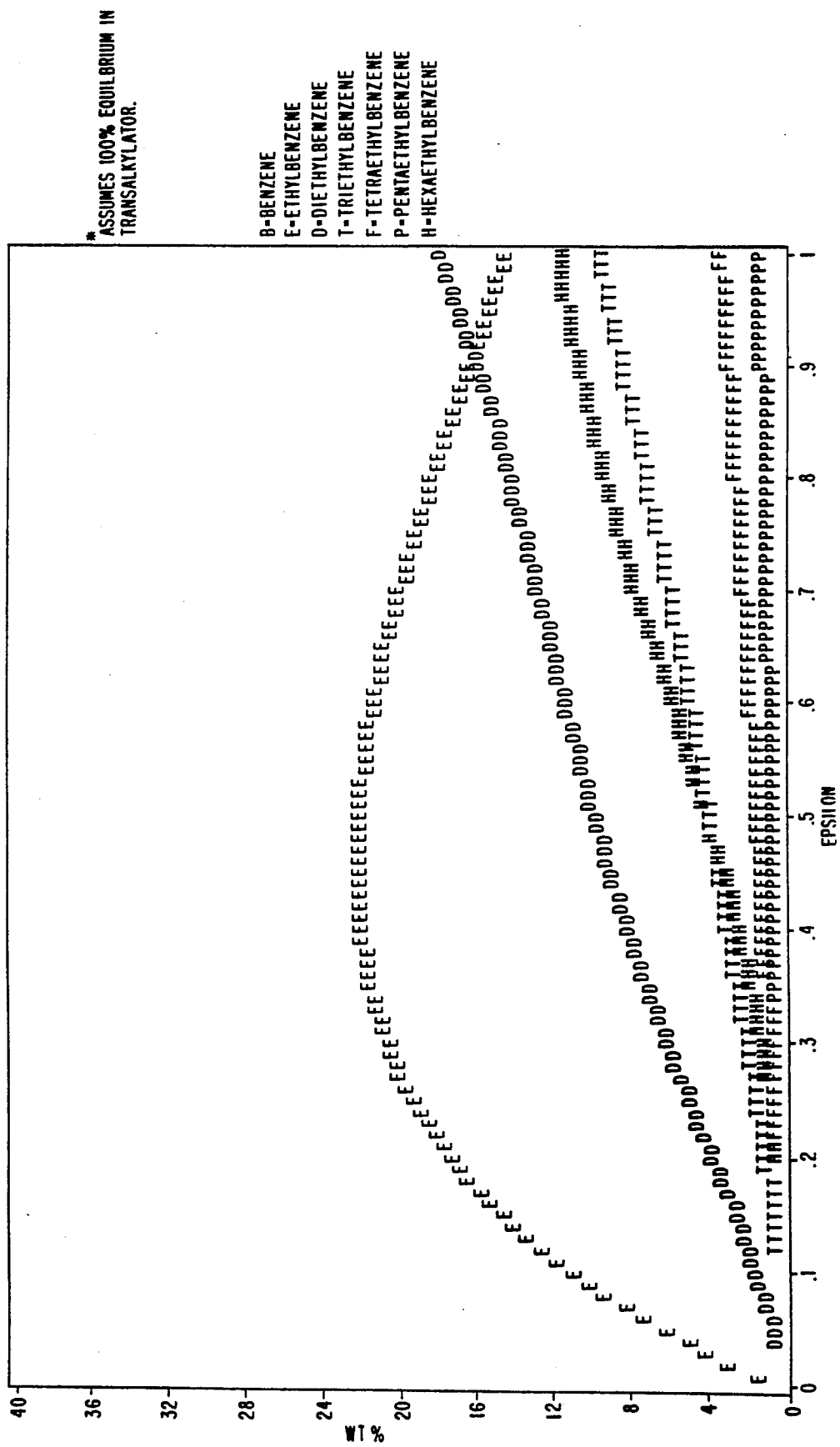
FIG. 8 is graph showing product distribution for a theoretical prior art process.
Figure 9:
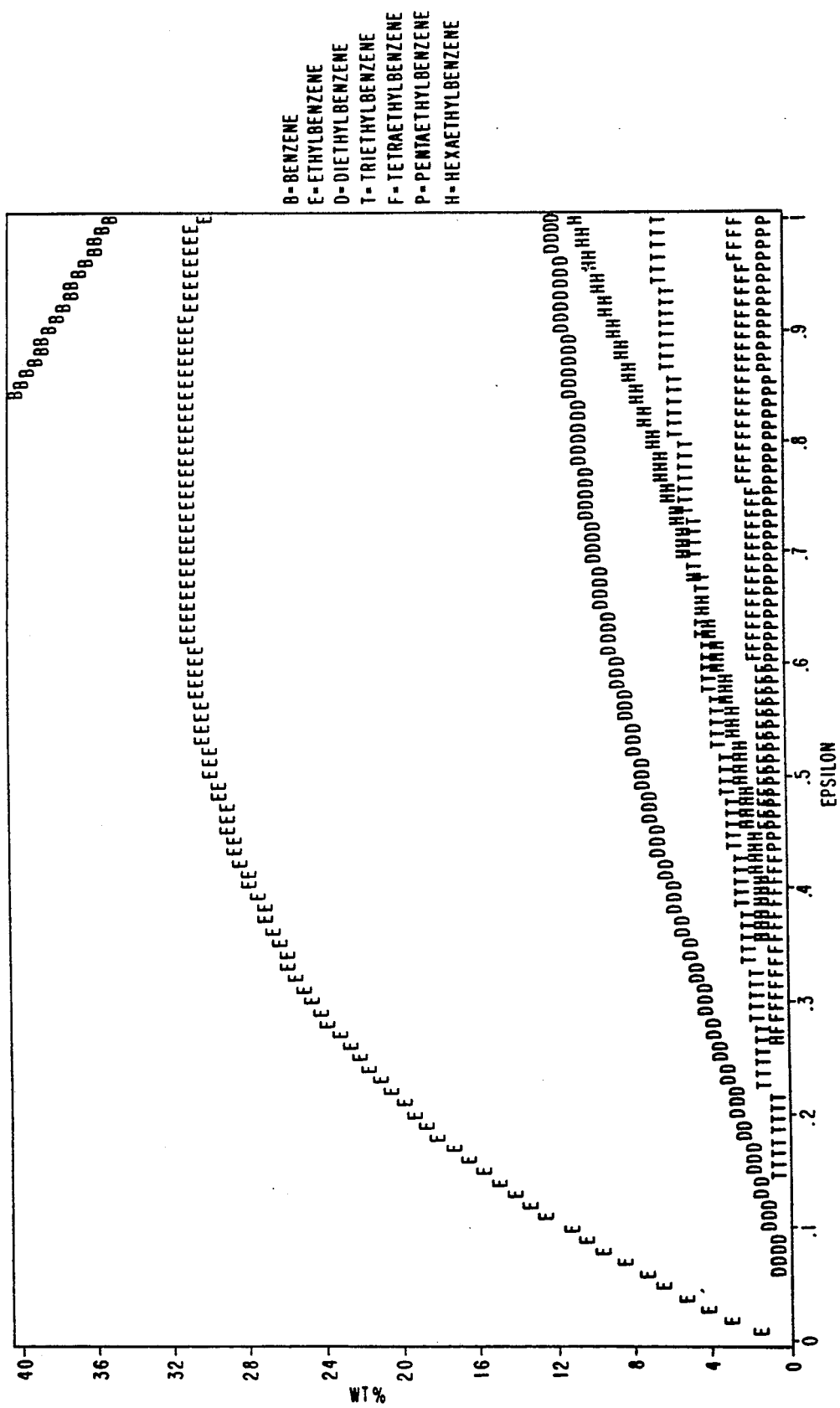
FIG. 9 is graph showing product distribution for a process conducted according to the present invention.
Figure 10:
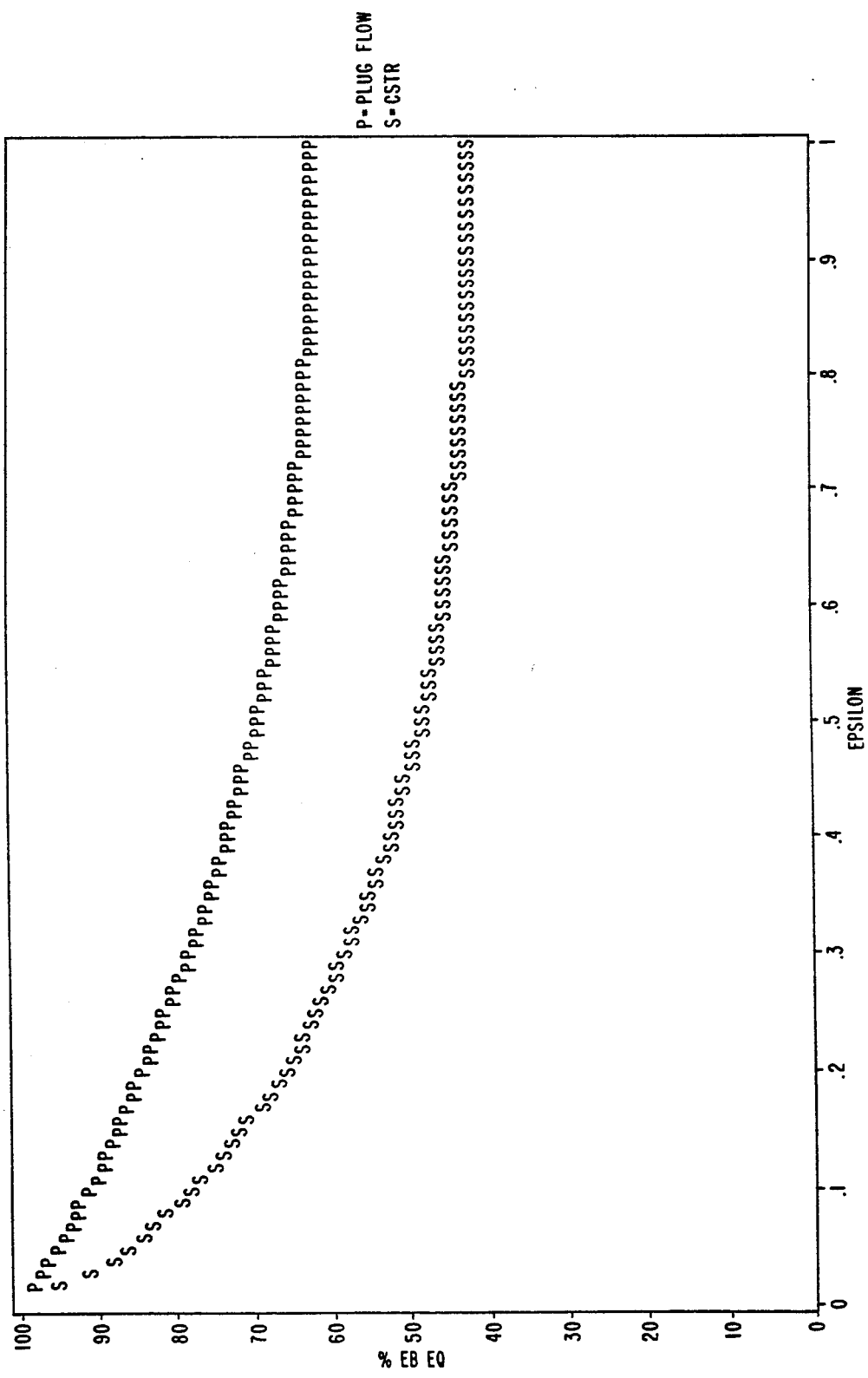
FIG. 10 is graph comparing a prior art process and a process according to the present invention.

The graphs in FIGS. 8, 9, and 10 present a theoretical comparison of a prior art process in which polyethylated benzenes are recycled to an alkylator reactor and a process according to the present invention in which produced polyethylated benzenes are not recycled to the alkylator reactor (as they are e.g. in feed line 310 to reactor 313 in FIG. 7). The abscissa of these graphs, epsilon, represents the process's ratio of ethylene to benzene in the reactor feed; e.g. 0.333 would indicate 1 molecule of ethylene per 3 molecules of benzene. These figures show the theoretical composition of an alkylator system's product as a function of epsilon where epsilon is the ratio of moles of ethyl groups to moles of aromatic rings in the alkylator. These figures represent processes which are closed loop processes between alkylator, transalkylator, and the finishing section with (and without) the recycle of polyethylated benzenes to the alkylator. In the processes reactions between ethylene and polyethylbenzenes to produce further polyethylbenzenes are more likely on an equal molar, basis than reactions between ethylene and benzene to produce ethylbenzene.

As the amount of ethylene increases in the prior art process of FIG. 8, the amount of ethylbenzene produced (the "E" line) begins to diminish after about 0.5. The vertical axis (FIGS. 8 and 9) is in units of weight % of a total of 100%.

In contrast, as shown in FIG. 9, with a process according to the present invention (e.g. as that shown in FIG. 7) not only does the amount of ethylbenzene produced exceed that of the prior art process of FIG. 8 at almost every point on the graph, it also does not diminish significantly. These graphs also show that the amount of polyethylated benzenes produced is greater in the prior art process.

The graph of FIG. 10 illustrates a comparison of the conversion of ethylene and benzene to ethylbenzene in a prior art process employing a larger reactor for both alkylation and transalkylation and a process according to the present invention employing a reactor according to the present invention as previously described. The "S" line is for a CSTR, a prior art continuous stirred tank reactor in which back mixing occurs; i.e. the undesirable formation of polyethylbenzenes occurring when ethylbenzenes and previously-formed polyethylbenzenes are recirculated in the tank reactor to again react with ethylene to form more polyethylbenzenes. Reaction times in such a reactor are typically 45 to 60 minutes. In a reactor according to the present invention, e.g. an eight-pass reactor, the total residence time in the reactor would be about 1 minute, or slightly less than 8 seconds (7.5 seconds) per pass. It is preferred that residence times be 15 seconds or less. This process is represented as the "P" line in FIG. 10 since it approaches plug-flow. As shown the conversion to ethylbenzene is significantly higher for the process (P) according to the present invention. The vertical axis in FIG. 10 represents % approach to equilibrium (equilibrium is the point at which no further reaction occurs).

FIGS. 11 and 12 present data obtained from a run of a single tube ("showtube") unit designed to indicate performance of ethylene injection, reaction, and heat transfer according to the present invention. The reactor for this unit was a 13.5 foot by 1.5 inch Hastelloy (TM) alloy pipe jacketed with a 2.5" diameter carbon steel pipe. Catalyst used for this run was a "red oil" complex prepared from aluminum metal, HCl gas and liquid ethylated benzenes. In this preferred embodiment the catalyst composition is prepared in a separate vessel as follows: aluminum metal (solid) fed at 5 weight %; liquid polyethylbenzene fed at 57 weight %; HCl gas fed at 38 weight %; fed at 75° C. and 30 p.s.i.g. with a contact time of 30 minutes. The aluminum concentration in the reactor was 442 parts per million. The reactants entered the showtube at about 195° C. and exited at 211° C. As can be seen in FIG. 12, essentially 100% of the ethylene was reacted with a Liquid Hourly Space Velocity of 330 hour$^{-1}$ (reciprocal of the residence time) at reaction conditions. Thermocouples were placed every 2" inches in the reaction tube and every 4" in the heat transfer medium surrounding the reaction tube. The pressure at the liquid entrance to the reaction tube was about 279.4 p.s.i.; that of the heat transfer medium was about 85.0 p.s.i.

As shown in FIG. 11, the reaction temperature approached 205° C. at a distance of about 46 inches into the tube and stayed between 205° C. and 210° C. until about 138 inches into the tube. The heat transfer medium in the shell (jacket) approached 150° C. 32 inches into the shell and remained around about 155° C. to about 160°. This fairly consistent temperature profile along the tube indicated that such a tube and such materials under these conditions would efficiently transfer heat from the reaction in the tube to the heat transfer material, heat which could then be utilized elsewhere in the process.

FIG. 14 presents data for a process to produce ethylbenzene in accordance with the present invention in a reactor system according to the present invention as as illustrated in FIGS. 1, 2 and 6a. For this process flow parameters are as follows:

| | |
|---|---|
| Shell internal temperature (heat transfer medium) | 207° C. |
| Benzene Feed temperature | 225° C. |
| Benzene Feed pressure | 357.5 psig |
| Product outlet pressure | 348.2 psig |
| Shell Pressure | 7.08 psig |
| Total Ethylene Feed Rate | 571 pounds/hour |
| Benzene Feed Rate | 4,495, pounds/hour |
| Catalyst Feed Rate | 8.77 pounds/hour |
| HCl (gas) Feed Rate | 11.08 pounds/hour |

This is an eight pass reactor (eight sets of six reaction tubes in each pass), and it has eight ethylene chambers with six spargers in communication with each chamber. The flow of ethylene in pounds per hour to each of these chambers is as follows:

1. 75.1
2. 74.8
3. 74.9
4. 74.9
5. 75.1
6. 75.0
7. 75.0

The exit temperature (in degrees celsius) of reactant materials and products for each pass (temperature measured at the end of each pass in the liquid chambers) is as follows:

1. 222.2
2. 225.5
3. 222.6
4. 225.5
5. 225.6
6. 226.2
7. 226.9
8. 226.5

The heat transfer coefficient for this process is 197 Btu/hour/ft$^2$/°F. The data in FIG. 14 as well as the data above indicate: (a) essentially all ethylene is reacted in each pass; (b) the temperature profile of the reactants is relatively flat which shows that the heat of the reaction is being uniformly and efficiently transferred to the heat transfer medium; (c) a uniform amount of ethylene is being fed to each of the eight passes; and (d) the epsilon in the alkylator is approximately 0.35, i.e., about one ethyl group per each three aromatic rings.

FIG. 15 presents data from a process according to the present invention in a reactor system according to the present invention as illustrated in FIGS. 5a and 7. For this process, flow parameters are as follows:

| | |
|---|---|
| Shell Internal Temperature | 216.6° C. |
| Ethylene Feed Temperature | 21.6° C. |
| Benzene Feed Temperature | 230.8° C. |
| Benzene Feed Pressure | 391.7 psig |
| Shell Pressure | 28.3 psig |
| Benzene Feed Rate | 353,100 pounds/hour |
| Catalyst Feed Rate | 2799 pounds/hour |
| HCl (gas) Feed Rate | 82.9 pounds/hour |
| Total Ethylene Feed Rate | 49,910 pounds/hour |
| Heat Transfer Coefficient (Btu/Hour/ft/$^2$/°F.) | 160 |
| ALCL$_3$ concentration (ppm) | 1805 |

Liquid temperatures for each pass of reactant materials are:

1. 218.9
2. 231.7
3. 213.7
4. 231.0
5. 235.3
6. 235.2
7. 233.1
8. 243.4

Ethylene feeds for each pass (1000 pounds/hour) are:

1. 6.24
2. 6.25
3. 6.24
4. 6.25
5. 6.24
6. 6.26
7. 6.25
8. 6.22

The data in FIG. 15 indicates: (a) essentially all ethylene is reacted in each pass; (b) the temperature profile of the reactants is relatively flat which shows that the heat of the reaction is being uniformly and efficiently transferred to the heat transfer medium; (c) a uniform amount of ethylene is being fed to each of the eight passes; and (d) epsilon in the alkylator is approximately 0.40, i.e., about two ethyl groups for each five aromatic rings.

In processes according to the present invention, e.g. FIG. 7, the alkylation and transalkylation steps are carried out separately and thus each step can be individually optimized. Because of the nature of reactors according to the present invention, the alkylation process can be optimized to reduce or negate the effects of back mixing which occur even in prior art processes in which transalkylation and alkylation are carried out in two separate reactors. In various prior art processes the catalyst concentration exceeds the solubility limit of catalyst in the liquid reactants producing a heterogeneous reaction mixture which contains two liquid phases (and therefore requires more catalyst). Two liquid phases moving down reaction tubes would perform inefficiently. Catalyst concentrations in preferred processes according to the present invention (e.g. in the particular processes described above) are below the solubility limit and are therefore homogeneous. The fact that in processes according to the present invention relatively high reaction temperatures are achievable contributes to the fact that the catalyst solubility limit is not exceeded (i.e., at higher temperatures the solubility limit is higher). Further contributing to the efficiency of processes according to the present invention is the relatively low temperature of the transalkylation reaction. It is preferred that this temperature be less than 75° C. and more than 40° C., with 65° C. preferred. This relatively cooler temperature will produce a two phase reactant mixture in the transalkylator. "Yield" is the ratio of ethylbenzene produced to the sum of ethylene and benzene fed to a plant. Yields for processes and alkylators according to this invention are very high. For example, in a process carried out in a reactor such as that of FIGS. 1 and 2 an alkylator yield of 99.7% (which would correspond to an overall plant yield of 99.6%) was achieved. For this particular process other parameters were as follows:

| | |
|---|---|
| Epsilon Alkylator/Transalkylator | .36/.45 |
| Ethylene Fixation (Amount of Ethylene reacted) | 100% |
| Benzene Feed Temperature | 222° C. |
| Liquid Product Temperature | 238° C. |
| Residence Time (Total In Reactor) | about 1 minute |
| Heat Transfer Coefficient | 168 |
| Liquid Product Outlet Pressure | 350 psig |
| Pressure Drop Through Tubes | 10.6 psi |
| Benzene Feed Rate | 4500 pounds/hour |
| Total Ethylene Feed Rate | 577 pounds/hour |
| Catalyst Concentration (parts per million) | 900 to 1200 |

This plant operated for 1131 hours with no evidence of fouling with residue (tar).

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. A turbulent alkylation method for producing ethylbenzene in an alkylation reactor vessel, the method comprising feeding gaseous ethylene under pressure into a gas chamber and then to gas spargers disposed horizontally in the reactor vessel and then from the gas spargers into reaction tubes disposed horizontally in the reactor vessel, feeding a liquid stream including catalyst and liquid benzene into a first liquid chamber and from the first liquid chamber into the reaction tubes in which the ethylene and benzene react exothermically producing a first stream with liquid benzene, catalyst, ethylbenzene and polyethylbenzenes as reaction products, the ethylene, catalyst and benzene flowing turbulently together in the reaction tubes and flowing horizontally there through, the ethylene, catalyst and liquid benzene having a residence time in each reaction tube of 15 seconds or less and the temperature in the reaction tubes maintained above 200 degrees Centigrade, flowing the first stream into a transalkylation reactor, a reaction in the transalkylation reactor producing a second stream with a higher ethylbenzene content and a lower polyethylbenzene than the first stream, the second stream containing catalyst, ethylbenzene, benzene, and polyethylbenzene, and the temperature in the transalkylation reactor maintained between 40 degrees Centigrade and 75 degrees Centigrade, flowing the second stream to separation means for separating out its components, including ethylbenzene, and pressure of the liquid stream decreasing in a first pressure drop between the first liquid chamber and the interior of the reaction tubes, pressure of the liquid stream decreasing in a second pressure drop as it flows across the first liquid chamber to each of the reaction tubes, the first pressure drop sufficiently greater than the second pressure drop so that a uniform amount of the liquid stream flows into each of the reaction tubes, the ratio of the first pressure drop to the second pressure drop greater than 10, and pressure of the gaseous ethylene decreasing in a primary pressure drop as it flows from the gas chamber and out of a hole in each sparger into a reaction tube, pressure of the gaseous ethylene decreasing in a secondary pressure drop as it flows across the gas chamber to each of the spargers, the primary pressure drop sufficiently greater than the secondary pressure drop so that a unifrom amount of gaseous ethylene flows into each of the spargers.

2. The method of claim 1 wherein the separation means includes an ethylbenzene finishing distillation tower, and the method also comprises flowing a heat transfer medium in heat exchange relationship with the horizontal reaction tubes in the reactor vessel to recover heat produced by the reaction of the ethylene and benzene, flowing the thus heated heat transfer medium to the ethylbenzene finishing distillation tower to provide heat for operating it.

3. The method of claim 2 comprising also feeding the second stream to a benzene recovery tower which produces a product stream containing benzene and water and a primary stream containing the ethylbenzene of the second stream, feeding the primary stream to the ethylbenzene finishing tower which produces a stream primarily of ethylbenzene and a stream primarily of polyethylbenzenes, feeding the product stream to a benzene dryer along with additional benzene having additional water, the benzene dryer producing a benzene stream which is primarily benzene and a water stream, feeding the benzene stream to a first heat exchanger through which flows the first stream prior to its flowing to the transalkylation reactor, and thereby heating the benzene stream, feeding the thus heated benzene stream into the reactor vessel, feeding the stream primarily of polyethylbenzenes to a polyethylbenzenes recovery tower which produces two streams, a stream of residue and a resultant stream of polyethylbenzenes, feeding the resultant stream of polyethylbenzenes to the transalkylation reactor, and flowing the first stream through a second heat exchanger in heat exchange relationship with the product stream from the benzene recovery tower before the product stream enters the benzene dryer to heat the product stream.

4. The method of claim 3 wherein the resultant stream combines with the first stream, and the combined stream is fed to the transalkylation reactor.

5. The method of claim 4 including feeding the second stream to a catalyst settler to remove some recyclable catalyst, feeding the second stream with some recyclable catalyst removed to a wash system having a water feed, the wash system producing a dead-catalyst-and-water stream and a new stream with the components of the second stream other than the materials in the dead-catalyst-and-water stream, and feeding the new stream to the separation means.

6. The method of claim 1 wherein the catalyst includes solid aluminum metal, liquid polyethylbenzenes, and hydrogen chloride gas.

7. The method of claim 1 wherein the liquid benzene entering the reactor vessel is at about 220 degrees Centigrade, gaseous ethylene is fed into the reactor vessel at about 25 degrees Centigrade, catalyst is fed into the reactor vessel at about 25 degrees Centigrade, and the first stream exits the reactor vessel at about 230 degrees Centigrade.

8. The method of claim 2 wherein the heated heat transfer medium is a liquid stream of polyethylbenzenes.

9. The method of claim 8 wherein the heat transfer medium is about 5% to about 50% vapor with the remainder liquid.

10. The method of claim 9 wherein the heat transfer medium is about 15% vapor and about 85% liquid.

11. The method of claim 2 wherein a major portion of each horizontal reaction tube is heated uniformly by reaction occurring therein and heat is transferred uniformly to the heat transfer medium.

12. The method of claim 1 wherein the horizontal vessel comprises a hollow reactor vessel having a first end, a second end, and a reaction product outlet from which products of the reaction flow from the reactor vessel, the horizontal reaction tubes each having an interior, an exterior surface, a first end and a second end and mounted within the reactor vessel extending horizontally from the first end of the reactor vessel to the second end of the reactor vessel, a first liquid chamber disposed at the first end of the reactor vessel for receiving liquid benzene and catalyst, the first end of the each of the reaction tubes communicating with the first liquid chamber so that the liquid benzene and catalyst flows with a pressure drop from the first chamber into the interior of the reaction tubes through its first end, a hollow sparger disposed horizontally and extending partially into each of the reaction tubes into and through which gaseous ethylene flows turbulently with a pressure drop into the interior of the reaction tubes for turbulently contacting and reacting therein with the liquid benzene in the presence of the catalyst, the gaseous ethylene, liquid benzene, catalyst, and products of the reaction flowing horizontally in the reaction tubes, the second ends of the reaction tubes in communication with the reaction product outlet so that reaction product of the reaction including ethylene will flow from the interior of the reaction tube, into and through the reaction product outlet and out of the reaction vessel, a gas chamber for receiving the gaseous ethylene, the hollow spargers disposed horizontally and communicating with and extending from the gas chamber so that gaseous ethylene flows from the gas chamber, into and through a hole in the portion of each of the spargers that extends into the reaction tubes, pressure of the liquid benzene and catalyst decreasing in a first pressure drop between the first liquid chamber and the interior of the reaction tubes, pressure of the liquid benzene and catalyst decreasing in a second pressure drop as it flows across the first liquid chamber to each of the reaction tubes, the first pressure drop sufficiently greater than the second pressure drop so that a uniform amount of the liquid benzene and catalyst flows into each of the reaction tubes, the ratio of the first pressure drop to the second pressure drop greater than 10, pressure of the gaseous ethylene decreasing in a primary pressure drop as it flows from the gas chamber and out of the hole in each sparger, pressure of the gaseous ethylene decreasing in a secondary pressure drop as it flows across the gas chamber to each of the spargers, the primary pressure drop sufficiently greater than the secondary pressure drop so that a uniform amount of gaseous ethylene flows into each of the spargers, and the reactant materials having a residence time in each reaction tube less than 8 seconds.

* * * * *